United States Patent
Havranek et al.

(10) Patent No.: US 10,017,832 B2
(45) Date of Patent: Jul. 10, 2018

(54) COMPOSITIONS AND METHODS FOR SITE SPECIFIC RECOMBINATION AT ASYMMETRIC SITES

(71) Applicant: Washington University, St. Louis, MO (US)

(72) Inventors: James J. Havranek, St. Louis, MO (US); Chi Zhang, St. Louis, MO (US); Joseph C. Corbo, St. Louis, MO (US); Connie A. Myers, St. Louis, MO (US); Robi D. Mitra, St. Louis, MO (US); Zongtai Qi, St. Louis, MO (US)

(73) Assignee: WASHINGTON UNIVERSITY, Saint Louis, MO (US)

( * ) Notice: Subject to any disclaimer, the term of this patent is extended or adjusted under 35 U.S.C. 154(b) by 1 day.

(21) Appl. No.: 15/247,452

(22) Filed: Aug. 25, 2016

(65) Prior Publication Data

US 2017/0058297 A1 Mar. 2, 2017

Related U.S. Application Data

(60) Provisional application No. 62/209,703, filed on Aug. 25, 2015.

(51) Int. Cl.
*C12N 15/85* (2006.01)
*C12N 9/12* (2006.01)

(52) U.S. Cl.
CPC .......... *C12Y 207/07* (2013.01); *C12N 9/1241* (2013.01); *C12N 15/85* (2013.01); *C12N 2800/30* (2013.01)

(58) Field of Classification Search
CPC ............................. C12Y 207/07; C12N 9/1241
See application file for complete search history.

(56) References Cited

U.S. PATENT DOCUMENTS

| | | | |
|---|---|---|---|
| 5,173,414 | A | 12/1992 | Lebkowski et al. |
| 5,658,776 | A | 8/1997 | Flotte et al. |
| 5,786,211 | A | 7/1998 | Johnson |
| 5,871,982 | A | 2/1999 | Wilson et al. |
| 6,258,595 | B1 | 7/2001 | Gao et al. |
| 7,198,951 | B2 | 4/2007 | Gao et al. |
| 2013/0039888 | A1 | 2/2013 | McCarty et al. |

FOREIGN PATENT DOCUMENTS

| | | | |
|---|---|---|---|
| CN | 102337292 B | * | 4/2013 |
| WO | 199513365 A1 | | 5/1995 |
| WO | 199513392 A1 | | 5/1995 |
| WO | 199617947 A1 | | 6/1996 |
| WO | 199706243 A1 | | 2/1997 |
| WO | 199708298 A1 | | 3/1997 |
| WO | 199709441 A2 | | 3/1997 |
| WO | 199721825 A1 | | 6/1997 |
| WO | 199911764 A2 | | 3/1999 |
| WO | 200183692 A2 | | 11/2001 |

OTHER PUBLICATIONS

Sternberg, N. et al., "Bacteriophage P1 Site-Specific Recombination: I. Recombination Between loxP Sites," J. Mol. Biol., Aug. 25, 1981, pp. 467-486, vol. 150, No. 4.
Studier, F., "Protein production by auto-induction in high-density shaking cultures," Protein Expr. Purif., May 2005, pp. 207-234, vol. 41, No. 1, Elsevier Inc.
Suzuki, E. et al., "VCre/VloxP and SCre/SloxP: new site-specific recombination systems for genome engineering," Nucl. Acids Res., 2011, pp. 1-11, vol. 39, No. 8, e49, Oxford University Press.
Szczepek, M. et al., "Structure-based redesign of the dimerization interface reduces the toxicity of zinc-finger nucleases," Nat. Biotechnol,, Jul. 2007, pp. 786-793, vol. 25, No. 7, Nature Publishing Group.
Tratschin, J-D. et al., "Adeno-Associated Virus Vector for High-Frequency Integration, Expression, and Rescue Genes in Mammalian Cells," Mol. Cell. Biol., Nov. 1985, pp. 3251-3260, vol. 5, No. 11, American Society for Microbiology.
Tratschin, J-D. et al., "A Human Parvovirus, Adeno-Associated Virus, as a Eucaryotic Vector: Transient Expression and Encapsidation of the Procaryotic Gene for Chloramphenicol Acetyltransferase," Mol. Cell. Biol., Oct. 1984, pp. 2072-2081, vol. 4, No. 10, American Society for Microbiology.
Turan, S. et al., "Recombinase-mediated cassette exchange (RMCE)—A rapidly-expanding toolbox for targeted genomic modifications," Gene, Feb. 15, 2013, pp. 1-27, vol. 515, No. 1, Elsevier B.V.
Wallace, H. et al., "Manipulating the Mouse Genome to Engineer Precise Functional Syntenic Replacements with Human Sequence," Cell, Jan. 12, 2007, pp. 197-209, vol. 128, Elsevier Inc.
Wang, Z. et al., "Adeno-associated virus serotype 8 efficiently delivers genes to muscle and heart," Nat. Biotech., Mar. 2005, pp. 321-328, vol. 23, No. 3, Nature Publishing Group.
Zincarelli, C. et al., "Analysis of AAV Serotypes 1-9 Mediated Gene Expression and Tropism in Mice After Systemic Injection," Mol. Ther., Jun. 2008, pp. 1073-1080, vol. 16, No. 6, The American Society of Gene Therapy.
Akimoto, M. et al., "Targeting of GFP to newborn rods by Nrl promoter and temporal expression profiling of flow-sorted photoreceptors," PNAS, Mar. 7, 2006, pp. 3890-3895, vol. 103, No. 10.
Anderson, R. et al., "Flp and Cre expressed from Flp-2A-Cre and Flp-IRES-Cre transcription units mediate the highest level of dual recombinase-mediated cassette exchange," Nucl. Acids Res., 2012, pp. 1-9, vol. 40, No. 8, e62, Oxford University Press.
Bethke, B. et al., "Segmental genomic replacement by Cre-mediated recombination: genotoxic stress activation of the p53 promoter in single-copy transformants," Nucl. Acids Res., 1997, pp. 2828-2834, vol. 25, No. 14, Oxford University Press.
Bolusani, S. et al., "Evolution of variants of yeast site-specific recombinase Flp that utilize native genomic sequences as recombination target sites," Nucl. Acids Res., 2006, pp. 5259-5269, vol. 34, No. 18, Oxford University Press.

(Continued)

*Primary Examiner* — Karen Cochrane Carlson
(74) *Attorney, Agent, or Firm* — Polsinelli PC

(57) ABSTRACT

The present invention relates to enzymes, compositions and methods for catalyzing site specific recombination at asymmetric sites.

20 Claims, 11 Drawing Sheets
(7 of 11 Drawing Sheet(s) Filed in Color)

(56) References Cited

OTHER PUBLICATIONS

Bouhassira, E. et al., "Transcriptional Behavior of LCR Enhancer Elements Integrated at the Same Chromosomal Locus by Recombinase-Mediated Cassette Exchange," Blood, Nov. 1, 1997, pp. 3332-3344, vol. 90, No. 9, The American Society of Hematology.
Buchholz, F. et al., "Alteration of Cre recombinase site specificity by substrate-linked protein evolution," Nat. Biotech., Nov. 1, 2001, pp. 1047-1052, vol. 19, Nature Publishing Group.
Carter, B., "Adeno-associated virus vectors," Curr. Opin. Biotechnol., Oct. 1992, pp. 533-539, vol. 3, No. 5, Current Biology Ltd.
Cong, L. et al., "Multiplex Genome Engineering Using CRISPR/Cas Systems," Science, Feb. 15, 2013, pp. 819-823, vol. 339, No. 6121.
Dantas, G. et al., "High-resolution Structural and Thermodynamic Analysis of Extreme Stabilization of Human Procarboxypeptidase by Computational Protein Design," J. Mol. Biol., Mar. 2, 2007, pp. 1209-1221, vol. 366, No. 4, Elsevier Ltd.
Duque, S. et al., "Intravenous Administration of Self-complementary AAV9 Enables Transgene Delivery to Adult Motor Neurons," Mol. Ther., Jul. 2009, pp. 1187-1196, vol. 17, No. 7, The American Society of Gene Therapy.
Elliott, B. et al., "Gene Conversion Tracts from Double-Strand Break Repair in Mammalian Cells," Mol. Cell. Biol., Jan. 1998, pp. 93-101, vol. 18, No. 1, American Society for Microbiology.
Foust, K. et al., "Intravascular AAV9 preferentially targets neonatal neurons and adult astrocytes," Nat. Biotechnol., Jan. 2009, pp. 59-65, vol. 27, No. 1, Nature America, Inc.
Gao, G. et al., "Clades of Adeno-Associated Viruses Are Widely Disseminated in Human Tissues," J. Virol., Jun. 2004, pp. 6381-6388, vol. 78, No. 12, American Society for Microbiology.
Gelato, K. et al., "Spatially Directed Assembly of a Heterotetrameric Cre-Lox Synapase Restricts Recombination Specificity," J. Mol. Biol., May 2, 2008, pp. 653-665, vol. 378, No. 3, Elsevier Ltd.
Gu, H. et al., "Independent Control of Immunoglobulin Switch Recombination at Individual Switch Regions Evidenced through Cre-loxP-Mediated Gene Targeting," Cell, Jun. 18, 1993, pp. 1155-1164, vol. 73, No. 6, Cell Press.
Hermonat, P. et al., "Use of adeno-associated virus as a mammalian DNA cloning vector: Transduction of neomycin resistance into mammalian tissue culture cells," PNAS, Oct. 1984, pp. 6466-6470, vol. 81.
Hirrlinger, J. et al., "Split-Cre Complementation Indicates Coincident Activity of Different Genes In Vivo," PLoS ONE, Jan. 2009, pp. 1-10, vol. 4, No. 1, e4286.
Hsiau, T. et al., "The Cis-regulatory Logic of the Mammalian Photoreceptor Transcriptional Network," PloS ONE, Jul. 25, 2007, pp. 1-16, vol. 2, No. 7, e643.
Hsu, P. et al., "Development and Applications of CRISPR-Cas9 for Genome Engineering," Cell, Jun. 5, 2014, pp. 1262-1278, vol. 157, Elsevier Inc.
Jinek, M. et al., "A Programmable Dual-RNA-Guided DNA Endonuclease in Adaptive Bacterial Immunity," Science, Aug. 17, 2012, pp. 816-821, vol. 337, No. 6096.
Kaplitt, M. et al., "Safety and tolerability of gene therapy with an adeno-associated virus (AAV) borne GAD gene for Parkinson's disease: an open label, phase I trial," Lancet, Jun. 23, 2007, pp. 2097-2105, vol. 369, No. 9579.
Karimova, M. et al., Vika/vox, a novel efficient and specific Cre/loxP-like site-specific recombination system, Nucl. Acids Res., 2012, pp. 1-13, vol. 41, No. 2, e37, Oxford University Press.
Laughlin, C. et al., "Cloning of infectious adeno-associated virus genomes in bacterial plasmids," Gene, Jul. 1983, pp. 65-73, vol. 23, No. 1.
Leaver-Fay, A. et al., "ROSETTA3: An Object-Oriented Software Suite for the Simulation and Design of Macromolecules," NIH Public Access Author Manuscript, available in PMC Jul. 7, 2014, pp. 1-27, Published in final edited form as: Methods Enzymol., 2011, pp. 545-574, vol. 487.
Lebkowski, J. et al., "Adeno-Associated Virus: a Vector System for Efficient Introduction and Integration of DNA into a Variety of Mammalian Cell Types," Mol. Cell. Biol., Oct. 1988, pp. 3988-3996, vol. 8, No. 10, American Society for Microbiology.
Loonstra, A. et al., "Growth inhibition and DNA damage induced by Cre recombinase in mammalian cells," PNAS, Jul. 31, 2001, pp. 9209-9214, vol. 98, No. 16.
Mali, P. et al., "RNA-Guided Human Genome Engineering via Cas9," Science, Feb. 15, 2013, pp. 823-826, vol. 339, No. 6121.
Marks, W. et al., "Safety and tolerability of intraputaminal delivery of CERE-120 (adeno-associated virus serotype 2-neurturin) to patients with idiopathic Parkinson's disease: an open-label, phase I trial;" Lancet Neurol., May 2008, pp. 400-408, vol. 7, No. 5.
Martin, S. et al., "The Order of Strand Exchanges in Cre-LoxP Recombination and its Basis Suggested by the Crystal Structure of a Cre-LoxP Holliday Junction Complex," J. Mol. Biol., May 24, 2002, pp. 107-127, vol. 319, No. 1, Elsevier Science Ltd.
McLaughlin, S. et al., "Adeno-Associated Virus General Transduction Vectors: Analysis of Proviral Structures," J. Virol., Jun. 1988, pp. 1963-1973, vol. 62, No. 6, American Society for Microbiology.
Montana, C. et al., "Quantifying the Activity of cis-Regulatory Elements in the Mouse Retina by Explant Electroporation," J. Vis. Exp., 2011, pp. 1-7, vol. 52, e2821.
Nunes-Duby, S. et al., "Similarities and differences among 105 members of the Int family of site-specific recombinases," Nucl. Acids Res., 1998, pp. 391-406, vol. 26, No. 2, Oxford University Press.
Pacak, C. et al., "Recombinant Adeno-Associated Virus Serotype 9 Leads to Preferential Cardiac Transduction In Vivo," Circ. Res., Aug. 18, 2006, pp. e3-e9, vol. 99, No. 4, American Heart Association, Inc.
Paul, R. et al., "Increased Viral Titer Through Concentration of Viral Harvests from Retroviral Packaging Lines," Human Gene Ther., 1993, pp. 609-615, vol. 4, Mary Ann Liebert, Inc. Publishers.
Perrin, P. et al., "An experimental rabies vaccine produced with a new BHK-21 suspension cell culture process: use of serum-free medium and perfusion-reactor system," Vaccine, 1995, pp. 1244-1250, vol. 13, No. 13, Elsevier Science Ltd., Great Britain.
Rothkamm, K. et al., "Pathways of DNA Double-Strand Break Repair during the Mammalian Cell Cycle," Mol. Cell. Biol., Aug. 2003, pp. 5706-5715, vol. 23, No. 16, American Society for Microbiology.
Ruffing, M. et al., "Mutations in the carboxy terminus of adeno-associated virus 2 capsid proteins affect viral infectivity: lack of an RGD integrin-binding motif," J. Gen. Virol., 1994, pp. 3385-3392, vol. 75, SGM, Great Britain.
Saleh-Gohari, N. et al., "Conservative homologous recombination preferentially repairs DNA double-strand breaks in the S phase of the cell cycle in human cells," Nucleic Acids Res, 2004, pp. 3683-3688, vol. 32, No. 12, Oxford University Press.
Samulski, R. et al., "Helper-Free Stocks of Recombinant Adeno-Associated Viruses: Normal Integration Does Not Require Viral Gene Expression," J. Virol., Sep. 1989, pp. 3822-3828, vol. 63, No. 9, American Society for Microbiology.
Samulski, R. et al., "Cloning of adeno-associated virus into pBR322: Rescue of intact virus from the recombinant plasmid in human cells," PNAS, Mar. 1982, pp. 2077-2081, vol. 79, No. 6, with Correction, p. 3901.
Santoro, S. et al., "Directed evolution of the site specificity of Cre recombinase," PNAS, Apr. 2, 2002, pp. 4185-4190, vol. 99, No. 7.
Saraf-Levy, T. et al., "Site-specific recombination of asymmetric lox sites mediated by a heterotetrameric Cre recombinase complex," Bioorg. Med. Chem., May 1, 2006, pp. 3081-3089, vol. 14, No. 9, Elsevier Ltd.
Sarkar, I. et al., "HIV-1 Proviral DNA Excision Using an Evolved Recombinase," Science, Jun. 29, 2007, pp. 1912-1915, vol. 316, No. 5833.

(56) References Cited

OTHER PUBLICATIONS

Sauer, B. et al., "DNA recombination with a heterospecific Cre homolog identified from comparison of the pac-c1 regions of P1-related phages," Nucl. Acids Res., 2004, pp. 6086-6095, vol. 32, No. 20, Oxford University Press.

Schlake, T. et al., "Use of Mutated FLP Recognition Target (FRT) Sites for the Exchange of Expression Cassettes at Defined Chromosomal Loci," Biochemistry, 1994, pp. 12746-12751, vol. 33, No. 43, American Chemical Society.

Seibler, J. et al., "Double-Reciprocal Crossover Mediated by FLP-Recombinase: A Concept and an Assay," Biochemistry, 1997, pp. 1740-1747, vol. 36, No. 7, American Chemical Society.

Senapathy, P. et al., "Molecular Cloning of Adeno-associated Virus Variant Genomes and Generation of Infectious Virus by Recombination in Mammalian Cells," J. Biol. Chem., Apr. 10, 1984, pp. 4661-4666, vol. 259, No. 7.

Sheren, J. et al., "A randomized library approach to identifying functional lox site domains for the Cre recombinase," Nucl. Acids Res., 2007, pp. 5464-5473, vol. 35, No. 16, Oxford University Press.

Soukharev, S. et al., "Segmental genomic replacement in embryonic stem cells by double lox targeting," Nucl. Acids Res., 1999, pp. i-viii, vol. 27, No. 18, e21, Oxford University Press.

Srivastava, A. et al., "Nucleotide Sequence and Organization of the Adeno-Associated Virus 2 Genome," J. Virol, Feb. 1983, pp. 555-564, vol. 45, No. 2, American Society for Mircrobiology.

\* cited by examiner

LL-LL

LL-LM

LM-LM

LM-ML

MM-LM

MM-MM

SEQUENCE LISTING

<160> NUMBER OF SEQ ID NOS: 6

<210> SEQ ID NO 1
<211> LENGTH: 343
<212> TYPE: PRT
<213> ORGANISM: Artificial Sequence
<220> FEATURE:
<223> OTHER INFORMATION: SYNTHESIZED

<400> SEQUENCE: 1

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
            35                  40                  45

Cys Arg Ser Trp Ala Ala Trp Cys Lys Leu Asn Asn Arg Lys Trp Phe
 50                  55                  60

Pro Ala Glu Pro Glu Asp Val Arg Asp Tyr Leu Leu Tyr Leu Gln Ala
 65                  70                  75                  80

Arg Gly Leu Ala Val Lys Thr Ile Gln Gln His Leu Gly Gln Leu Asn
                 85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
            115                 120                 125

Glu Arg Ala Lys Gln Ala Leu Ala Phe Glu Arg Thr Asp Phe Asp Gln
130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
            195                 200                 205

Val Glu Lys Ala Leu Ser Leu Gly Val Thr Lys Leu Val Glu Arg Trp
            210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
            275                 280                 285

His Ser Ala Arg Val Gly Ala Ala Arg Asp Met Ala Arg Ala Gly Val
            290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 2
<211> LENGTH: 343
<212> TYPE: PRT
<213> ORGANISM: Artificial Sequence
<220> FEATURE:
<223> OTHER INFORMATION: SYNTHESIZED

<400> SEQUENCE: 2

Met Ser Asn Leu Leu Thr Val His Gln Asn Leu Pro Ala Leu Pro Val
 1               5                  10                  15

Asp Ala Thr Ser Asp Glu Val Arg Arg Asn Leu Met Arg Met Phe Glu
                20                  25                  30

Leu Arg Arg Ala Phe Ser Glu His Thr Trp Lys Met Leu Leu Ser Val
            35                  40                  45

Cys Arg Ser Trp Ala Ala Trp Cys Lys Leu Asn Asn Arg Lys Trp Phe
            50                  55                  60

Pro Ala Glu Pro Glu Asp Val Arg Asp Tyr Leu Leu Tyr Leu Gln Ala
 65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Leu Asn Val Asp Ala Gly
            115                 120                 125

Glu Arg Ala Lys Gln Ala Leu Ala Phe Glu Arg Thr Asp Phe Asp Gln
130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
            195                 200                 205

Val Glu Lys Ala Leu Ser Leu Gly Val Thr Lys Leu Val Glu Arg Trp
210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
            275                 280                 285

His Ser Ala Arg Val Gly Ala Ala Arg Asp Met Ala Arg Ala Gly Val
            290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Glu Leu Leu Glu Asp Gly Asp
            340

<210> SEQ ID NO 3
<211> LENGTH: 343
<212> TYPE: PRT
<213> ORGANISM: Artificial Sequence
<220> FEATURE:
<223> OTHER INFORMATION: SYNTHESIZED

<400> SEQUENCE: 3

Met Ser Asn Leu Leu Thr Val His Gln Asn Leu Pro Ala Leu Pro Val
 1               5                  10                  15

Asp Ala Thr Ser Asp Glu Val Arg Lys Asn Leu Met Asp Met Phe Arg
                20                  25                  30

Asp Arg Gln Ala Phe Ser Glu His Thr Trp Lys Met Leu Leu Ser Val
            35                  40                  45

Cys Arg Ser Trp Ala Ala Trp Cys Lys Leu Asn Asn Arg Lys Trp Phe
            50                  55                  60

```
Pro Ala Glu Pro Asp Asp Val Lys Asp Tyr Leu Glu Tyr Leu Gln Ala
 65                  70                  75                  80

Arg Gly Leu Ala Val Lys Thr Ile Gln Gln His Leu Gly Gln Leu Asn
                 85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
        115                 120                 125

Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Arg Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340
```

<210> SEQ ID NO 4
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 4
ataacttcgt atagcataca ttatacgaag ttat                                34

<210> SEQ ID NO 5
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 5
ataactctat atagcataca ttatatagag ttat                                34

```
<210> SEQ ID NO 6
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 6
ataacttcgt atagcataca ttatatagag ttat                              34
```

COMPOSITIONS AND METHODS FOR SITE SPECIFIC RECOMBINATION AT ASYMMETRIC SITES

CROSS REFERENCE TO RELATED APPLICATIONS

This application claims the benefit of U.S. Provisional Application No. 62/209,703, filed Aug. 25, 2015, the disclosure of which is hereby incorporated by reference in its entirety.

GOVERNMENTAL RIGHTS

This invention was made with government support under R01GM101602 and R01EY018826 awarded by the NIH. The government has certain rights in the invention.

FIELD OF THE INVENTION

The present invention relates to enzymes, compositions and methods for catalyzing site specific recombination at asymmetric sites.

BACKGROUND OF THE INVENTION

Cre recombinase forms a tetrameric complex that splices DNA molecules containing the 34-bp recombination target (RT) site loxP (Sternberg and Hamilton, 1981, J Mol Biol, 150, 467-86), recombining two DNA molecules in trans to accomplish an insertion or translocation event, or in cis to achieve either gene excision or inversion, depending on the relative orientation of the loxP sites. Cre recombinase has been used to generate conditional gene knockouts, where a gene of interest is flanked by loxP sites ('floxed') (Gu et al., 1993, Cell, 73, 1155-64). Expression of Cre recombinase under the control of promoters that are specific for particular tissues or developmental stages abrogates gene function by physical excision from the genome. The utility of this system depends on the functional autonomy of Cre recombinase: the enzyme requires no other factors to splice DNA, and is capable of modifying genomes in non-replicating cells, where the efficacy of gene conversion via double-strand break (DSB) induced homologous recombination is expected to be low (Saleh-Gohari and Helleday, 2004, Nucleic Acids Res, 32, 3683-8; Rothkamm et al., 2003, Mol Cell Biol, 23, 5706-15).

Another application for Cre recombinase is recombination-mediated cassette exchange (RMCE) (Bouhassira et al., 1997, Blood, 90, 3332-3344), also known as double-reciprocal crossover (Schlake and Bode, 1994, Biochemistry, 33, 12746-12751; Seibler and Bode, 1997, Biochemistry, 36, 1740-1747) or double-lox replacement (Bethke and Sauer, 1997, Nucleic Acids Res, 25, 2828-34; Soukharev et al., 1999, Nucleic Acids Res, 27, e21). In this approach, (reviewed in Turan et al., 2013, Gene, 515, 1-27) recombination between DNA molecules that share two neighboring heterologous RT sites accomplishes the exchange of the bounded genetic interval (the cassette) between the sites. This has been demonstrated using both Flp and Cre recombinase with heterologous RT variants (Bethke and Sauer, 1997, Nucleic Acids Res, 25, 2828-34; Bouhassira et al., 1997, Blood, 90, 3332-3344), as well as simultaneously with Cre and the Flp recombinases (Anderson et al., 2012, Nucleic Acids Res, 40, e62). Although RMCE has so far only been demonstrated with wild-type recombinase proteins and RT sites, the approach has many attractive features as a tool for genome engineering. First, it has a higher efficiency for gene conversion than does Cre-mediated insertion, as it does not require survival of insertional events that are susceptible to reversal by excision (Bethke and Sauer, 1997, Nucleic Acids Res, 25, 2828-34). Second, the cassettes that are exchanged are precisely demarcated, yielding truly 'scarless' genomic surgery. Third, the process requires less Cre protein than recombinational insertion, resulting in less cytotoxicity (Bethke and Sauer, 1997, Nucleic Acids Res, 25, 2828=34). Finally, the autonomy of Cre as a recombinase suggests that RMCE could prove to be effective in terminally differentiated cells, in contrast to strategies for gene conversion that rely upon homology directed repair.

One impediment to broader use of Cre recombinase is the inflexibility of the binding site specificity. In contrast to DNA binding proteins whose specificity derives from the assembly of small recognition modules such as zinc finger or TAL effector domains, Cre recombinase interacts with DNA through large interfaces that defy a modular decomposition. Accordingly, broader application of the Cre recombinase system is limited by the fixed sequence preferences of Cre, which are determined by both the direct DNA contacts and the homotetrameric arrangement of the Cre monomers. Thus, there is a need in the art for a method to break the symmetry of Cre recombinase such that its use may be expanded to broader applications. As such, there is an unmet need for recombination systems that are not limited to wild type recognition sites and moreover that are not restricted to palindromic symmetry of recognition sites, thus enabling recombination of any desired recombination site.

SUMMARY OF THE INVENTION

In an aspect, the disclosure provides an isolated enzyme comprising two distinct subunits A and B. The A subunit comprises one or more mutations at K25, D29, R32, D33, Q35, E123 and R337 relative to SEQ ID NO:1 and the B subunit comprises one or more mutations at E69, R72, L76, E123, E308 relative to SEQ ID NO:1 and the isolated enzyme is a tetramer. Specifically, the A subunit comprises the mutations: K25R, D29R, R32E, D33L, Q35R, E123L and R337E relative to SEQ ID NO:1 and the B subunit comprises the mutations: E69D, R72K, L76E and E308R relative to SEQ ID NO:1 and the isolated enzyme is a tetramer.

In another aspect, the disclosure provides an isolated polynucleotide encoding at least one polypeptide. The polypeptide comprises subunit A comprising one or more mutations at K25, D29, R32, D33, Q35, E123 and R337 relative to SEQ ID NO:1, subunit B comprising one or more mutations at E69, R72, L76, E123, E308 relative to SEQ ID NO:1, or combinations thereof. The isolated polynucleotide is encompassed in a recombinant vector that expresses the polypeptide and is selected from the group consisting of: a naked plasmid, a plasmid within a liposome, a retroviral vector, an AAV vector, or a recombinant adenoviral vector. Specifically, the polypeptide comprises subunit A comprising the mutations: K25R, D29R, R32E, D33L, Q35R, E123L and R337E relative to SEQ ID NO:1, subunit B comprising the mutations: E69D, R72K, L76E and E308R relative to SEQ ID NO:1, or combinations thereof.

In still another aspect, the disclosure provides a method for mediating asymmetric site-specific recombination in a nucleic acid. The method comprises contacting an isolated enzyme of the disclosure with a nucleic acid. The isolated enzyme recognizes asymmetric sites on the nucleic acid and cleaves the asymmetric sites. The asymmetric site-specific recombination is selected from the group consisting of inversion, excision, insertion and translocation.

In still yet another aspect, the disclosure provides a method for mediating recombination-mediated cassette exchange (RMCE) in a cell. The method comprises contacting an isolated enzyme of the disclosure and an exogenous DNA molecule with a cellular endogenous genome. The isolated enzyme recognizes asymmetric sites on the cellular endogenous genome and the RMCE occurs between the cellular endogenous genome and the exogenous DNA molecule such that the exogenous DNA molecule is integrated by recombination between the two asymmetric sites into a predetermined locus within the cellular genome.

BRIEF DESCRIPTION OF THE FIGURES

The application file contains at least one drawing executed in color. Copies of this patent application publication with color drawing(s) will be provided by the Office upon request and payment of the necessary fee.

(FIG. 1A) Direct repeats of the loxP site can be recombined to excise the intervening genetic interval (downward arrow). This reaction is also catalyzed in the reverse direction, yielding a genetic insertion (upward arrow). For thermodynamic reasons, the excision reaction is favored, and insertion events occur with low frequency. (FIG. 1B) Inverted loxP repeats can be recombined to yield an inversion of the bracketed DNA. (FIG. 1C) Recombination at pairs of distinct RT sites gives rise to exchange of the intervening genetic 'cassette'. (FIG. 1D) Cre recombinase is a homotetramer in its functional complex (wt Cre), imparting a preference for a symmetric RT as a consequence. As a first step to achieving recombination at asymmetric sites, we desire an orthogonal engineered interface between Cre monomers (eng Cre). We seek to construct a novel homotetramer Cre mutant with monomer-monomer interfaces that, while functional, are incompatible with the wild-type protein. Combining wild-type and engineered half-interfaces gives rise to two distinct mutants that cannot form functional complexes (mutants A and B). Combining the two mutants (denoted by 'M' here and in later figures) can reconstitute a functional heterotetrameric complex, which contains two wild-type and two engineered interfaces.

(FIG. 2A) The arrangement of Cre monomers on a loxP Holliday junction. The nucleic acid is shown as grey spheres, and each Cre monomer is rendered in a separate color. The largest area of contact is indicated with a cyan oval on a side view of the complex (left side), and likewise the salt bridge that was inverted, shown in a bottom view (right side). (FIG. 2B) A set of interacting residues across the monomer-monomer interface was selected by eye for computational redesign (positions 25, 29, 32, 33, 35, 69, 72, 76, 119, and 123). The experimentally determined conformations of the sidechains at these positions are shown (PDB code: 1 KBU) {Martin et al., 2002, J Mol Biol, 319, 107-27}). In a third round and rational design, positions 35 and 123 were mutated to hydrophobic residues. (FIG. 2C) A putative salt bridge between a glutamate at position 308 and an arginine at position 337 is observed in the wild-type crystal structure. (FIG. 2D) The predicted model of the monomer-monomer interface after computational redesign is shown. The amino acids at positions 29 and 32 switch their electrostatic charge relative to wild-type, position 33 switches from charged to hydrophobic, and positions 76 and 35 switch from uncharged to charged amino acids. (FIG. 2E) A putative model for the charge swap at positions 308 and 337 preserves a salt bridge, but with an change in polarity.

(FIG. 3A) In vitro recombinase assay. A 0.7 kb linear DNA substrate with direct repeats of the loxP site (orange triangles) is incubated with wild-type or mutant Cre recombinase. The activity of functional Cre complexes results in production of a 0.5 kb circular product and a 0.2 kb linear product through intra-molecular excision. (FIG. 3B) In vitro assay results. Lane 1: DNA substrate alone; lane 2: wild-type Cre; lanes 3-5: $1^{st}$ round redesigned Cre mutants Cre-A1, Cre-B1 and a mixture of the two (CreA1+CreB1); lanes 6-8: $2^{nd}$ round redesigned Cre mutants Cre-A2, Cre-B2 and a mixture of the two (Cre-A2+Cre-B2); lanes 9-10: $3^{rd}$ round mutant Cre-A3 and a mixture of Cre-A3+Cre-B2. All Cre-B mutants are inactive in isolation. Cre-A mutants progressively lose homotetramer activity through the three rounds of design. (FIG. 3C) In vitro substrates for asymmetric recombination target site experiments. RT half-sites in the linear DNA substrate described in panel (A) were systematically varied to incorporate the M7 sequence {Santoro and Schultz, 2002, Proc Natl Acad Sci USA, 99, 4185-4190}. LoxP and M7 half-sites are rendered as green and red boxes, and abbreviated by the letters L and M, respectively. Combinations ranged from entirely loxP (LL-LL, the same as in panel (A)) to entirely M7 (MM-MM), including hybrid RT sites situated as both direct (LM-LM) and inverted (LM-ML) repeats. (FIG. 3D) The effect of controlled assembly of heterotetrameric Cre complexes. Each of the mixed loxP/M7 substrates was incubated with a pair of recombinases, one with mutations that recognize the M7 RT halfsite (Cre-C2#4) and the other with preference for the loxP half-site. In the left panel, the two proteins have no additional mutations to control complex formation. In the middle and right panels, recombinases with different RT specificities are combined with the Cre-A3 and Cre-B2 mutations, with both possible combinations tested. The restriction of permissible substrates by the Cre-A3 and Cre-B2 mutations are consistent with a requirement for an (ABAB) heterotetramer to achieve recombinase activity.

(FIG. 4A) Diagram of the Cre-reporter cell line. The Cre-reporter cassette was inserted into the Rosa26 locus, in the intron between endogenous exons 1 and 2. In the cassette, a red-fluorescent protein (RFP) is preceded by a floxed stop codon and followed by the woodchuck post-transcriptional regulatory element (WPRE). (FIG. 4B) Plasmids with the hbb minimal promoter driving expression of different Cre variants either alone or augmented with the CMV or SP1 enhancers were co-transfected into Ai14 mouse embryonic stem (ES) cells containing a fluorescent reporter cassette. The same total amount of DNA was used for all transfections, and 3 independent transfections were performed for each Cre variant. The number of RFP positive cells was measured by flow cytometry. A total of 7000 cells were sorted after each transfection. The average number of RFP positive cells for each Cre variant or combination of variants is shown. For Cre-B2, Cre-A3, and Cre-A3, cell counts were less than five for all promoter constructs (Table 2).

(FIG. 5E) Quantification of activity of electroporated constructs relative to wild-type Cre.

(FIG. 6A) Round 2 and round 3 mutations were combined to create Cre-E123L-E308R and Cre-E123LE-R337E. In vitro assays as described in FIG. 3 indicated that these mutants do not form an obligate heterotetrameric pair. (FIG. 6B) Again using the in vitro assays as described in FIG. 3, it was shown that Cre-C2#4 is slightly promiscuous, and can recombine loxP sites when incubated with DNA substrate for a long period of time. It is also interesting to note that, because the four Cre monomers work cooperatively to recombine the DNA target, wild-type Cre and Cre-C2#4 homotetramers recombined most of the loxP/M7 hybrid sites on their own.

FIG. 7A shows Cre recombinase activity using only the Cre-B3 mutant. FIG. 7B shows Cre recombinase activity using the Cre-A3 and Cre-B3 mutant.

DETAILED DESCRIPTION OF THE INVENTION

Figure 1A:
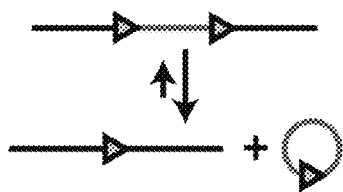
FIG. 1A, FIG. 1B, FIG. 1C and FIG. 1D depict schematics of genomic applications of Cre recombinase. Depending on the number and relative orientation of the loxP sites, Cre recombinase can perform deletion, inversion, insertion or exchange of genetic content.
Figure 1B:
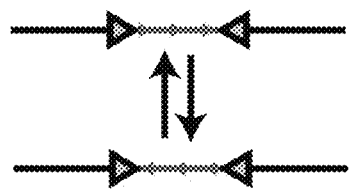

Cre recombinase catalyzes the cleavage and religation of DNA at loxP sites. The enzyme is a homotetramer in its functional state, and the symmetry of the protein complex enforces a pseudo-palindromic symmetry upon the loxP sequence. The Cre-lox system is a powerful tool for many researchers, particularly those working in mouse genetics. However, broader application of the system is limited by the fixed sequence preferences of Cre, which are determined by both the direct DNA contacts and the homotetrameric arrangement of the Cre monomers. As a first step towards achieving recombination at arbitrary asymmetric target sites, the inventors have broken the symmetry of the Cre tetramer assembly. The inventors have engineered an alternative interface between Cre monomers that is functional yet incompatible with the wild-type interface. Wild-type and engineered interface halves can be mixed to create two distinct Cre mutants, neither of which are functional in isolation, but which can form an active heterotetramer when combined. When these distinct mutants possess different DNA specificities, control over complex assembly directly discourages recombination at unwanted half-site combinations, enhancing the specificity of asymmetric site recombination. The engineered Cre mutants exhibit this assembly pattern in a variety of contexts, including mammalian cells. The availability of obligate heterotetrameric mutants allows for controlled assembly of Cre monomers whose DNA specificities may be altered independently.

I. Composition

In one aspect, the disclosure encompasses a composition comprising an isolated polynucleotide encoding at least one polypeptide, the polypeptide comprising subunit A comprising one or more mutations at K25, D29, R32, D33, Q35, E123 and R337 relative to SEQ ID NO:1, subunit B comprising one or more mutations at E69, R72, L76, E123, E308 relative to SEQ ID NO:1, or combinations thereof, wherein the isolated polynucleotide is encompassed in a recombinant vector that expresses the polypeptide and is selected from the group consisting of: a naked plasmid, a plasmid within a liposome, a retroviral vector, an AAV vector, or a recombinant adenoviral vector. Specifically, subunit A comprises the mutations: K25R, D29R, R32E, D33L, Q35R, E123L and R337E relative to SEQ ID NO:1 and subunit B comprises the mutations: E69D, R72K, L76E and E308R relative to SEQ ID NO:1.

In another aspect, the invention encompasses a composition comprising (i) a first isolated polynucleotide encoding at least one polypeptide, the polypeptide comprising subunit A comprising one or more mutations at K25, D29, R32, D33, Q35, E123 and R337 relative to SEQ ID NO:1, wherein the isolated polynucleotide is encompassed in a recombinant vector that expresses the polypeptide comprising subunit A; and (ii) a second isolated polynucleotide encoding at least one polypeptide, the polypeptide comprising subunit B comprising one or more mutations at E69, R72, L76, E123, E308 relative to SEQ ID NO:1, wherein the isolated polynucleotide is encompassed in a recombinant vector that expresses the polypeptide comprising subunit B. Specifically, subunit A comprises the mutations: K25R, D29R, R32E, D33L, Q35R, E123L and R337E relative to SEQ ID NO:1 and subunit B comprises the mutations: E69D, R72K, L76E and E308R relative to SEQ ID NO:1.

(a) Isolated Enzyme

Figure 1C:
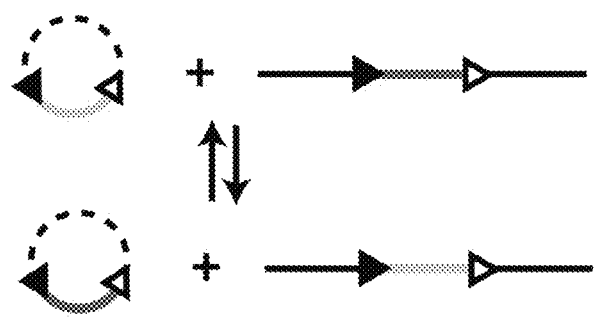
Figure 1D:
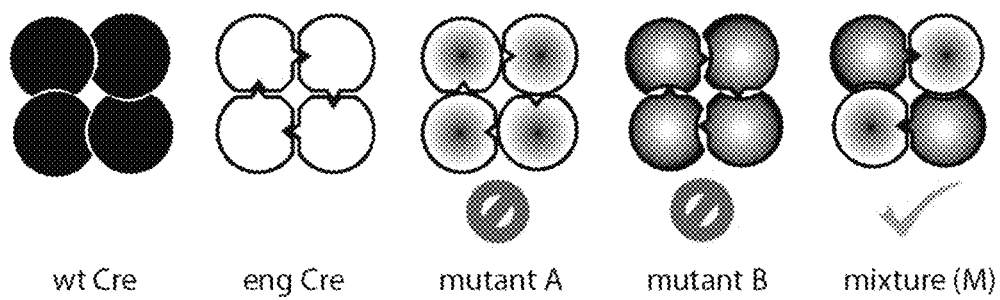

The present disclosure encompasses an isolated subunit A enzyme comprising one or more mutations at K25, D29, R32, D33, Q35, E123 and R337 relative to SEQ ID NO:1. Specifically, the mutations at D29, R32, D33, Q35, E123 and R337 relative to SEQ ID NO:1 alter the charge of the original amino acids. For example, if the original amino acid is positive, the mutation may include a negative or neutral amino acid. Or, if the original amino acid is negative, the mutation may include a positive or neutral amino acid. Or, if the original amino acid is neutral, the mutation may include a positive or neutral amino acid. Non-limiting examples of positive amino acids include arginine (R), histidine (H), and lysine (K). Non-limiting examples of negative amino acids include aspartic acid (D) and glutamic acid (E). Non-limiting examples of neutral amino acids include serine (S), threonine (T), asparagine (N), glutamine (Q), alanine (A), valine (V), isoleucine (I), leucine (L), methionine (M), phenylalanine (F), tyrosine (Y), tryptophan (W), cysteine (C), selenocysteine (U), glycine (G), and proline (P). In an embodiment, D29 is mutated to a positive or neutral amino acid, R32 is mutated to a negative or neutral amino acid, D33 is mutated to a positive or neutral amino acid, Q35 is mutated to a positive or negative amino acid, E123 is mutated to a positive or neutral amino acid, and/or R337 is mutated to a negative or neutral amino acid. In certain embodiments, K25 is mutated to another positive amino acid, D29 is mutated to a positive amino acid, R32 is mutated to a negative amino acid, D33 is mutated to a neutral amino acid, Q35 is mutated to a positive amino acid, E123 is mutated to a neutral amino acid, and/or R337 is mutated to a negative amino acid. In an embodiment, the present disclosure encompasses an isolated subunit A enzyme comprising the mutations: D29 is mutated to a positive amino acid, R32 is mutated to a negative amino acid, and R337 is mutated to a negative amino acid. In other embodiments, the present disclosure encompasses an isolated subunit A enzyme comprising one or more mutations selected from the group consisting of: K25R, D29R, R32E, D33L, Q35R, E123L and R337E relative to SEQ ID NO:1. In another embodiment, the present disclosure encompasses an isolated subunit A enzyme comprising the mutations: D29R, R32E, and R337E relative to SEQ ID NO:1. In still other embodiments, the present disclosure encompasses an isolated subunit A enzyme comprising the mutations: D29R, R32E, D33L, Q35R, E123L and R337E relative to SEQ ID NO:1. In a specific embodiment, the present disclosure encompasses an isolated subunit A enzyme comprising the mutations: K25R, D29R, R32E, D33L, Q35R, E123L and R337E relative to SEQ ID NO:1. In an embodiment, the present disclosure encompasses an isolated subunit A enzyme comprising at least 80% identity to SEQ ID NO:2. For example, the isolated enzyme may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:2.

The present disclosure encompasses an isolated subunit B enzyme comprising one or more mutations at E69, R72, L76, E123, E308 relative to SEQ ID NO:1. Specifically, the mutations at L76, E123 and E308 relative to SEQ ID NO:1 alter the charge of the original amino acids. For example, if the original amino acid is positive, the mutation may include a negative or neutral amino acid. Or, if the original amino acid is negative, the mutation may include a positive or neutral amino acid. Or, if the original amino acid is neutral, the mutation may include a positive or neutral amino acid. Non-limiting examples of positive amino acids include, arginine (R), histidine (H), and lysine (K). Non-limiting examples of negative amino acids include aspartic acid (D) and glutamic acid (E). Non-limiting examples of neutral amino acids include serine (S), threonine (T), asparagine (N), glutamine (Q), alanine (A), valine (V), isoleucine (I), leucine (L), methionine (M), phenylalanine (F), tyrosine (Y), tryptophan (W), cysteine (C), selenocysteine (U), glycine (G), and proline (P). In an embodiment, L76 is mutated to a negative or positive amino acid, E123 is mutated to a neutral or negative amino acid, and/or E308 is mutated to a positive or neutral amino acid. In a specific embodiment, L76 is mutated to a negative amino acid, E123 is mutated to a neutral amino acid, and/or E308 is mutated to a positive amino acid. In another specific embodiment, E308 is mutated to a positive amino acid. Additionally, the mutations at E69 and R72 relative to SEQ ID NO:1 substitute the charged amino acid for another amino acid of the same charge. For example, E69 is mutated to aspartic acid (D) and/or R72 is mutated to histidine (H) or lysine (K). In an embodiment, the present disclosure encompasses an isolated subunit B enzyme comprising one or more mutations selected from the group consisting of: E69D, R72K, L76E, E123L, and E308R relative to SEQ ID NO:1. In an embodiment, the present disclosure encompasses an isolated subunit B enzyme comprising the mutation: E308R relative to SEQ ID NO:1. In another embodiment, the present disclosure encompasses an isolated subunit B enzyme comprising the mutations: R72K, L76E and E308R relative to SEQ ID NO:1. In a specific embodiment, the present disclosure encompasses an isolated subunit B enzyme comprising the mutations: E69D, R72K, L76E and E308R relative to SEQ ID NO:1. In another specific embodiment, the present disclosure encompasses an isolated subunit B enzyme comprising the mutations: E69D, R72K, L76E, E123L and E308R relative to SEQ ID NO:1. In an embodiment, the present disclosure encompasses an isolated subunit B enzyme comprising at least 80% identity to SEQ ID NO:3. For example, the isolated enzyme may have about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100% identity to SEQ ID NO:3.

Additionally, the present disclosure encompasses an isolated enzyme comprising two distinct subunits A and B, wherein the A subunit and the B subunit are as described above and wherein the isolated enzyme is a tetramer. Specifically, the present disclosure encompasses an isolated enzyme comprising two distinct subunits A and B, wherein the A subunit comprises the mutations: K25R, D29R, R32E, D33L, Q35R, E123L and R337E relative to SEQ ID NO:1 and the B subunit comprises the mutations: E69D, R72K, L76E and E308R relative to SEQ ID NO:1 and wherein the isolated enzyme is a tetramer. The isolated enzyme comprising two distinct subunits A and B has been designed such that only an ABAB heterotetrameric complex results in a functional enzyme. Importantly, a homotetrameric complex of subunit A or subunit B results in a non-functional enzyme.

In an aspect, the isolated enzyme of the invention is a Cre recombinase comprising the aforementioned mutations. Cre recombinase is a tyrosine recombinase enzyme derived from the P1 Bacteriophage. The enzyme uses a topoisomerase I like mechanism to carry out site specific recombination events. The enzyme (38 kDa) is a member of the integrase family of site specific recombinase and it is known to catalyze the site specific recombination event between two DNA recognition sites (loxP sites). This 34 base pair (bp) loxP recognition site consists of two 13 bp palindromic sequences which flank an 8 bp spacer region represented by SEQ ID NO:4. The products of Cre-mediated recombination at loxP sites are dependent upon the location and relative orientation of the loxP sites. Two separate DNA species both containing loxP sites can undergo fusion as the result of Cre mediated recombination. DNA sequences found between two loxP sites are said to be “floxed”. In this case the products of Cre mediated recombination depends upon the orientation of the loxP sites. DNA found between two loxP sites oriented in the same direction will be excised as a circular loop of DNA whilst intervening DNA between two loxP sites that are opposingly orientated will be inverted. The active site of the Cre enzyme consists of the conserved catalytic triad residues Arg 173, His 289, Arg 292 as well as the conserved nucleophilic residues Tyr 324 and Trp 315. Cre does not form a shared active site between separate subunits and all the residues that contribute to the active site are found on a single subunit. Consequently when two Cre molecules bind at a single loxP site, two active sites are present. Cre mediated recombination requires the formation of a synapse in which two Cre-LoxP complexes associate to form what is known as the synapse tetramer in which 4 distinct active sites are present. One impediment to broader use of Cre recombinase is the inflexibility of the binding site specificity (i.e. the 34 bp loxP recognition site). However, the inventors have overcome this impediment with the development of the Cre recombinase subunits A and B comprising specific mutations. Subunit A comprises the mutations: K25R, D29R, R32E, D33L, Q35R, E123L and R337E relative to SEQ ID NO:1 and subunit B comprises the mutations: E69D, R72K, L76E and E308R relative to SEQ ID NO:1. The recited mutations results in the formation of a Cre recombinase tetramer comprising two A subunits and two B subunits as depicted in FIG. 1D. Subunit A and subunit B can be designed to have specificity for different target sites. The heterotetrameric complex enables the specific and reliable targeting of the mutant Cre recombinase to asymmetric recombination sites.

The terms "asymmetric recombination site" as used herein is used to describe a non-palindromic DNA element comprising a first and a second DNA sequence, also termed hereinafter non-palindromic halves. The two non-palindromic halves flank a spacer region which confers directionality to the recombination site and hence to the recombination reaction. The first and second DNA sequences correspond to two recognition sites. Cre recombinases which can catalyze recombination at various recognition sites are known in the art. See for example, Buchholz and Stewart, *Nature biotechnology* 2001, 19, 1047-1052; Santoro and Schultz, *Proc Natl Acad Sci USA* 2002, 99, 4185-4190; and Sarkar et al., *Science* 2007, 316, 1912, all of which are hereby incorporated by reference in their entirety. In an embodiment, the two non-palindromic halves are recognized by a tetrameric enzyme of the invention comprising two A subunits and two B subunits. In certain embodiments, one non-palindromic half is not similar to a natural recognition site, such as the natural loxP site. In another embodiment, one non-palindromic half is a loxP site. In still another embodiment, one non-palindromic half is a M7 site. In a specific embodiment, one non-palindromic half is a loxP site and one non-palindromic half is a M7 site. In an exemplary embodiment, the asymmetric recombination site comprises SEQ ID NO:6 (ATAACTTCGTATAGCATACATTATATAGAGTTAT).

The Cre recombinase tetramer comprising two A subunits and two B subunits is capable of mediating a site-specific recombination between two predetermined recombination sites, wherein the recombination sites are asymmetric recombination sites comprising two non-palindromic halves flanking a spacer region. Stated another way, the Cre recombinase tetramer comprising two A subunits and two B subunits is capable of mediating a site-specific recombination between two asymmetric recombination sites, wherein the asymmetric recombination sites comprise two non-palindromic halves flanking a spacer region. As used herein, the terms "site-specific recombination" and "asymmetric recombination" are used interchangeably herein to describe recombination between two asymmetric recombination sites. The present invention encompasses any form of recombination event including, without limitation, recombination between recombination sites that are in a cis or trans location. In the cis situation, the orientation of the recombination sites may be the same or the opposite. In the case of trans localization, the DNA strands involved can be linear or circular. In the case of cis location of two recombination sites, the outcome of the recombination may be excision or inversion of an intervening sequence. In the case of trans located recombination sites, the outcome may be insertion of one DNA into another or translocation between two DNA molecules. Accordingly, the asymmetric recombination may result in inversion, excision, insertion or translocation of DNA. The recombination event may occur between the cellular endogenous genome and an exogenous DNA molecule or may occur between only the endogenous genome. In an embodiment where the recombination event occurs between the cellular endogenous genome and an exogenous DNA molecule, the exogenous DNA molecule may be integrated by recombination between the two recombination sites into a predetermined locus within the cellular genome. Such a recombination event may be referred to as recombination-mediated cassette exchange (RMCE).

(b) Enzyme Construct

In an aspect, the present invention provides an enzyme construct. An enzyme construct of the invention is a polynucleotide sequence encoding at least one polypeptide, the polypeptide comprising subunit A, subunit B or a combination thereof. As used herein, the terms "polynucleotide sequence of the invention" and "enzyme construct" are interchangeable. The present invention also provides isolated polypeptides encoded by enzyme constructs, vectors comprising enzyme constructs, and isolated cells comprising said vectors.

i. Polynucleotide Sequence

An enzyme construct of the invention is a polynucleotide sequence encoding at least one polypeptide, the polypeptide comprising subunit A, subunit B or a combination thereof. In certain embodiments, the enzyme construct is a polynucleotide sequence encoding at least one polypeptide, the polypeptide comprising subunit A. In another embodiment, the enzyme construct is a polynucleotide sequence encoding at least one polypeptide, the polypeptide comprising subunit B. In still another embodiment, the enzyme construct is a polynucleotide sequence encoding at least two polypeptides, the polypeptides comprising subunit A and subunit B.

When more than one polypeptide is encoded by a polynucleotide of the invention, the polynucleotide may comprise more than one promoters operably linked to each polynucleotide encoding a polypeptide. By way of non-limiting example, a polynucleotide encoding a polypeptide comprising subunit A may be operably linked to a first promoter and a polynucleotide encoding a polypeptide comprising subunit B may be operably linked to a second promoter. The first and second promoter may be the same or different. Promoters are described in more detail below.

Alternatively, when more than one polypeptide is encoded by a polynucleotide of the invention, the polynucleotide may be operably linked to a single promoter. In such an embodiment, several strategies common in the art may be used to generate more than one expression product. By way of non-limiting example, a splicing signal, internal ribosomal entry site (IRES) or proteolytic cleavage site may be inserted between the polynucleotides encoding the polypeptides. By way of non-limiting example, a polynucleotide encoding a polypeptide comprising subunit A and subunit B operably linked to a single promoter may further comprise a splicing signal, IRES or proteolytic cleavage site between the coding regions of subunit A and subunit B.

In each of the above embodiments, "subunit A" and "subunit B" may be as described in detail above in Section I(a), which are hereby incorporated by reference into this section.

Polynucleotide sequences of the invention may be produced from nucleic acids molecules using molecular biological methods known to in the art. Any of the methods known to one skilled in the art for the amplification of polynucleotide fragments and insertion of polynucleotide fragments into a vector may be used to construct the polynucleotide sequences of the invention. These methods may include in vitro recombinant DNA and synthetic techniques and in vivo recombinations (See Sambrook et al. Molecular Cloning, A Laboratory Manual, Cold Spring Harbor Laboratory; Current Protocols in Molecular Biology, Eds. Ausubel, et al., Greene Publ. Assoc., Wiley-Interscience, NY).

ii. Polypeptide Sequence

In another aspect, the present invention provides one or more isolated polypeptide(s) encoded by a polynucleotide sequence of the invention. Polynucleotide sequences of the invention are described in detail in Section I(b)i, and are hereby incorporated by reference into this section. In an embodiment, an isolated polypeptide of the invention comprises subunit A. In another embodiment, an isolated polypeptide of the invention comprises subunit B. In still another embodiment, an isolated polypeptide of the invention comprises subunit A linked to subunit B. In such an embodiment, an isolated polypeptide may comprise subunit A attached to subunit B via a linker stretching between the C-terminus of subunit A to the N-terminus of subunit B. Alternatively, an isolated polypeptide may comprise subunit A attached to subunit B via a linker stretching between the C-terminus of subunit B to the N-terminus of subunit A. Subunit A and subunit B may be separated via cleavage before or after isolation of the polypeptide. In still another aspect, an isolated polypeptide of the invention comprises subunits A and subunits B in the form of a tetramer.

Isolated polypeptides of the invention may be produced from nucleic acids molecules using molecular biological methods known to in the art. Generally speaking, a polynucleotide sequence encoding the polypeptide is inserted into a vector that is able to express the polypeptide when introduced into an appropriate host cell. Appropriate host cells include, but are not limited to, bacterial, yeast, insect, and mammalian cells. Once expressed, polypeptides may be obtained from cells of the invention using common purification methods. For example, if the polypeptide has a secretion signal, expressed polypeptides may be isolated from cell culture supernatant. Alternatively, polypeptides lacking a secretion signal may be purified from inclusion bodies and/or cell extract. Polypeptides of the invention may be isolated from culture supernatant, inclusion bodies or cell extract using any methods known to one of skill in the art, including for example, by chromatography (e.g., ion exchange, affinity, particularly by affinity for the specific antigen after Protein A, and sizing column chromatography), centrifugation, differential solubility, e.g. ammonium sulfate precipitation, or by any other standard technique for the purification of proteins; see, e.g., Scopes, "Protein Purification", Springer Verlag, N.Y. (1982). Isolation of polypeptides is greatly aided when the polypeptide comprises a purification moiety.

iii. Regulation

In certain aspects, the expression of a polynucleotide sequence of the invention and/or a polypeptide of the invention may be regulated. Such regulation may allow control over when and where an enzyme construct functions.

Expression vectors typically contain one or more of the following elements: promoters, terminators, ribosomal binding sites, and RES. Such elements may be used to control the expression of an enzyme construct of the invention. Expression of the nucleic acid molecules of the invention may be regulated by a second nucleic acid sequence so that the molecule is expressed in a host transformed with the recombinant DNA molecule. For example, expression of the nucleic acid molecules of the invention may be controlled by any promoter/enhancer element known in the art. The term "promoter", as used herein, may mean a synthetic or naturally-derived molecule that is capable of conferring, activating or enhancing expression of a nucleic acid. A promoter may be constitutive, inducible/repressible or cell type specific. In certain embodiments, the promoter may be constitutive. Non-limiting examples of constitutive promoters include CMV, UBC, EF1α, SV40, PGK, CAG, CBA/CA-GGS/ACTB, CBh, MeCP2, U6 and H1. In other embodiments, the promoter may be an inducible promoter. The inducible promoter may be selected from the group consisting of: tetracycline, heat shock, steroid hormone, heavy metal, phorbol ester, adenovirus E1A element, interferon, and serum inducible promoters. In different embodiments, the promoter may be cell type specific. For example, cell type specific promoters for neurons (e.g. syapsin), astrocytes (e.g. GFAP), oligodendrocytes (e.g. myelin basic protein), microglia (e.g. CX3CR1), neuroendocrine cells (e.g. chromogranin A), muscle cells (e.g. desmin, Mb), or cardiomyocytes (e.g. alpha myosin heavy-chain promoter) could be used. In an exemplary embodiment, a promoter may be the Nrl (rod photoreceptor-specific) promoter or the HBB (haemoglobin beta) promoter. A promoter may further comprise one or more specific transcriptional regulatory sequences to further enhance expression and/or to alter the spatial expression and/or temporal expression of a nucleic acid. Non-limiting examples of enhancer include the CMV enhancer and the SP1 enhancer.

In an embodiment where more than one polypeptide is encoded by a polynucleotide of the invention and the polynucleotide comprises more than one promoters operably linked to each polynucleotide encoding a polypeptide, the promoters may be the same or different. The term "operably linked," as used herein, means that expression of a nucleic acid sequence is under the control of a promoter with which it is spatially connected. A promoter may be positioned 5' (upstream) of the nucleic acid sequence under its control. The distance between the promoter and a nucleic acid sequence to be expressed may be approximately the same as the distance between that promoter and the native nucleic acid sequence it controls. As is known in the art, variation in this distance may be accommodated without loss of promoter function.

iv. Vector

In another aspect, the present invention provides a vector comprising an enzyme construct of the invention. As used herein, a vector is defined as a nucleic acid molecule used as a vehicle to transfer genetic material. Vectors include but are not limited to, plasmids, phasmids, cosmids, transposable elements, viruses (bacteriophage, animal viruses, and plant viruses), and artificial chromosomes (e.g., YACs), such as retroviral vectors (e.g. derived from Moloney murine leukemia virus vectors (MoMLV), MSCV, SFFV, MPSV, SNV etc), lentiviral vectors (e.g. derived from HIV-1, HIV-2, SIV, BIV, FIV etc.), adenoviral (Ad) vectors including replication competent, replication deficient and gutless forms thereof, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

The vector may have a high copy number, an intermediate copy number, or a low copy number. The copy number may be utilized to control the expression level for the enzyme construct, and as a means to control the expression vector's stability. In one embodiment, a high copy number vector may be utilized. A high copy number vector may have at least 31, 35, 40, 45, 50, 55, 60, 65, 70, 75, 80, 85, 90, 95, or 100 copies per bacterial cell. In other embodiments, the high copy number vector may have at least 100, 125, 150, 175, 200, 225, 250, 275, 300, 325, 350, 375, or 400 copies per host cell. In an alternative embodiment, a low copy number vector may be utilized. For example, a low copy number vector may have one or at least two, three, four, five, six, seven, eight, nine, or ten copies per host cell. In another embodiment, an intermediate copy number vector may be used. For instance, an intermediate copy number vector may have at least 10, 11, 12, 13, 14, 15, 16, 17, 18, 19, 20, 21, 22, 23, 24, 25, 26, 27, 28, 29, or 30 copies per host cell.

A nucleic acid encoding an enzyme construct may also be operably linked to a nucleotide sequence encoding a selectable marker. A selectable marker may be used to efficiently select and identify cells that have integrated the exogenous nucleic acids. Selectable markers give the cell receiving the exogenous nucleic acid a selection advantage, such as resistance towards a certain toxin or antibiotic. Suitable examples of antibiotic resistance markers include, but are not limited to, those coding for proteins that impart resistance to kanamycin, spectomycin, neomycin, gentamycin (G418), ampicillin, tetracycline, chloramphenicol, puromycin, hygromycin, zeocin, and blasticidin.

In some embodiments, the vector may also comprise a transcription cassette for expressing reporter proteins. By way of example, reporter proteins may include a fluorescent protein, luciferase, alkaline phosphatase, beta-galactosidase, beta-lactamase, horseradish peroxidase, and variants thereof.

An expression vector encoding an enzyme construct may be delivered to the cell using a viral vector or via a non-viral method of transfer. Viral vectors suitable for introducing nucleic acids into cells include retroviruses, adenoviruses, adeno-associated viruses, rhabdoviruses, and herpes viruses. Non-viral methods of nucleic acid transfer include naked nucleic acid, liposomes, and protein/nucleic acid conjugates. An expression construct encoding an enzyme construct that is introduced to the cell may be linear or circular, may be single-stranded or double-stranded, and may be DNA, RNA, or any modification or combination thereof.

An expression construct encoding an enzyme construct may be introduced into the cell by transfection. Methods for transfecting nucleic acids are well known to persons skilled in the art. Transfection methods include, but are not limited to, viral transduction, cationic transfection, liposome transfection, dendrimer transfection, electroporation, heat shock, nucleofection transfection, magnetofection, nanoparticles, biolistic particle delivery (gene gun), and proprietary transfection reagents such as Lipofectamine, Dojindo Hilymax, Fugene, jetPEI, Effectene, or DreamFect.

Upon introduction into the cell, an expression construct encoding an enzyme construct may be integrated into a chromosome. In some embodiments, integration of the expression construct encoding an enzyme construct into a cellular chromosome may be achieved with a mobile element. The mobile element may be a transposon or a retro-element. A variety of transposons are suitable for use in the invention. Examples of DNA transposons that may be used include the Mu transposon, the P element transposons from *Drosophila*, and members of the Tc1/Mariner superfamily of transposons such as the sleeping beauty transposon from fish. A variety of retroelements are suitable for use in the invention and include LTR-containing retrotransposons and non-LTR retrotransposons. Non-limiting examples of retrotransposons include Copia and gypsy from *Drosophila melanogaster*, the Ty elements from *Saccharomyces cerevisiae*, the long interspersed elements (LINEs), and the short interspersed elements (SINEs) from eukaryotes. Suitable examples of LINEs include Li from mammals and R2Bm from silkworm.

Integration of the exogenous nucleic acid into a cellular chromosome may also be mediated by a virus. Viruses that integrate nucleic acids into a chromosome include retroviruses. A variety of retroviruses are suitable for use in the invention. Retroviral vectors may either be replication-competent or replication-defective. The retroviral vector may be an alpharetrovirus, a betaretrovirus, a gammaretrovirus, a deltaretrovirus, an epsilonretrovirus, a lentivirus, or a spumaretrovirus. In an embodiment, the retroviral vector may be a lentiviral vector. The lentiviral vector may be derived from human, simian, feline, equine, bovine, or lentiviruses that infect other mammalian species. Non-limiting examples of suitable lentiviruses includes human immunodeficiency virus (HIV), simian immunodeficiency virus (SIV), feline immunodeficiency virus (FIV), bovine immunodeficiency virus (BIV), and equine infectious anemia virus (EIAV).

Integration of an expression construct encoding an enzyme construct into a chromosome of the cell may be random. Alternatively, integration of an expression construct encoding an enzyme construct may be targeted to a particular sequence or location of a chromosome. In general, the general environment at the site of integration may affect whether the integrated expression construct encoding an enzyme construct is expressed, as well as its level of expression.

The virus may be altered to have tropism for a specific cell type. In certain embodiments, the virus may be altered to have tropism for cells of the central nervous system. For example, the virus may be altered to have tropism for glial cells. Alternatively, the virus may be altered to have tropism for neuronal cells.

Cells transfected with the expression construct encoding an enzyme construct generally will be grown under selection to isolate and expand cells in which the nucleic acid has integrated into a chromosome. Cells in which the expression construct encoding an enzyme construct has been chromosomally integrated may be maintained by continuous selection with the selectable marker as described above. The presence and maintenance of the integrated exogenous nucleic acid sequence may be verified using standard techniques known to persons skilled in the art such as Southern blots, amplification of specific nucleic acid sequences using the polymerase chain reaction (PCR), and/or nucleotide sequencing.

Nucleic acid molecules are inserted into a vector that is able to express the fusion polypeptides when introduced into an appropriate host cell. Appropriate host cells include, but are not limited to, bacterial, yeast, insect, and mammalian cells.

In certain embodiments, a vector-comprising an enzyme construct of the invention is an adeno-associated viral (AAV) vector. Adeno-associated virus (AAV) vectors may be from human or nonhuman primate AAV serotypes and variants thereof. Suitable adeno-associated viruses include AAV type 1, AAV type 2, AAV type 3, AAV type 4, AAV type 5, AAV type 6, AAV type 7, AAV type 8, AAV type 9, AAV type 10, and AAV type 11. Adeno-associated virus (AAV) is a replication-deficient parvovirus, the single-stranded DNA genome of which is about 4.7 kb in length including 145 nucleotide inverted terminal repeat (ITRs). The nucleotide sequence of the AAV serotype 2 (AAV2) genome is presented in Srivastava et al., *J Virol*, 45: 555-564 (1983) as corrected by Ruffing et al., *J Gen Virol*, 75:

3385-3392 (1994). Cis-acting sequences directing viral DNA replication, encapsidation/packaging and host cell chromosome integration are contained within the ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, *Current Topics in Microbiology and Immunology*, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA such as a gene cassette containing a promoter, a DNA of interest and a polyadenylation signal. The rep and cap proteins may be provided in trans. Another significant feature of AAV is that it is an extremely stable and hearty virus. It easily withstands the conditions used to inactivate adenovirus, making cold preservation of AAV less critical. AAV may even be lyophilized. Finally, AAV-infected cells are not resistant to superinfection.

Multiple serotypes of AAV exist and offer varied tissue tropism. Known serotypes include, for example, AAV1, AAV2, AAV3, AAV4, AAV5, AAV6, AAV7, AAV8, AAV9, AAV10 and AAV11. AAV9 is described in U.S. Pat. No. 7,198,951 and in Gao et al., *J. Virol.*, 78: 6381-6388 (2004). Advances in the delivery of AAV6 and AAV8 have made possible the transduction by these serotypes of skeletal and cardiac muscle following simple systemic intravenous or intraperitoneal injections. See, Pacak et al., *Circ. Res.*, 99(4): 3-9 (1006) and Wang et al., *Nature Biotech.*, 23(3): 321-328 (2005). The use of some serotypes of AAV to target cell types within the central nervous system, though, has required surgical intraparenchymal injection. See, Kaplitt et al., *Lancet* 369: 2097-2105 (2007); Marks et al., *Lancet Neurol* 7: 400-408 (2008); and Worgall et al., *Hum Gene Ther* (2008). AAV serotypes such as AAV5 and AAV8 have been identified as particularly efficacious in targeting CNS tissues, and serotype AAV9 has been demonstrated to cross the blood-brain barrier.

An adeno-associated viral (AAV) vector is a plasmid comprising a recombinant AAV genome. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep and cap genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. Production of pseudotyped rAAV is disclosed in, for example, WO 01/83692 which is incorporated by reference herein in its entirety. In an exemplary embodiment, a vector is based on the AAV2 serotype. In another exemplary embodiment, a vector is based on the AAV9 serotype (see, for example, Foust et al., *Nature Biotechnology*, 27: 59-65 (2009); Duque et al., *Mol. Ther.* 17: 1187-1196 (2009); Zincarelli et al., *Mol. Ther.*, 16: 1073-1080 (2008); and U.S. Patent Publication No. 20130039888).

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbiol. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. No. 5,786,211; U.S. Pat. No. 5,871,982; and U.S. Pat. No. 6,258,595. The foregoing documents are hereby incorporated by reference in their entirety herein, with particular emphasis on those sections of the documents relating to rAAV production.

The invention thus provides packaging cells that produce infectious rAAV. In another aspect, the invention provides rAAV (i.e., infectious encapsidated rAAV particles) comprising a rAAV genome of the invention. In some embodiments of the invention, the rAAV genome is a self-complementary genome.

v. Isolated Cell

In another aspect, the present invention provides an isolated cell comprising a vector of the invention. The cell may be a prokaryotic cell or a eukaryotic cell. Appropriate cells include, but are not limited to, bacterial, yeast, insect, and mammalian cells.

In some embodiments, the isolated host cell comprising a vector of the invention may be used to produce a polypeptide encoded by an enzyme construct of the invention. Generally, production of a polypeptide of the invention involves transfecting isolated host cells with a vector comprising an enzyme construct and then culturing the cells so that they transcribe and translate the desired polypeptide. The isolated host cells may then be lysed to extract the expressed polypeptide for subsequent purification. "Isolated host cells" according to the invention are cells which have been removed from an organism and/or are maintained in vitro in substantially pure cultures. A wide variety of cell types can be used as isolated host cells of the invention, including both prokaryotic and eukaryotic cells. Isolated cells include, without limitation, bacterial cells, fungal cells, yeast cells, insect cells, and mammalian cells.

In one embodiment, the isolated host cell is characterized in that after transformation with a vector of the invention, it produces the desired polypeptide for subsequent purification. Such a system may be used for protein expression and purification as is standard in the art. In some embodiments, the host cell is a prokaryotic cell. Non-limiting examples of suitable prokaryotic cells include *E. coli* and other Enterobacteriaceae, *Escherichia* sp., *Campylobacter* sp., *Wolinella* sp., *Desulfovibrio* sp. *Vibrio* sp., *Pseudomonas* sp. *Bacillus* sp., *Listeria* sp., *Staphylococcus* sp., *Streptococcus* sp., *Peptostreptococcus* sp., *Megasphaera* sp., *Pectinatus* sp., *Selenomonas* sp., *Zymophilus* sp., *Actinomyces* sp., *Arthrobacter* sp., *Frankia* sp., *Micromonospora* sp., *Nocardia* sp., *Propionibacterium* sp., *Streptomyces* sp., *Lactobacillus* sp., *Lactococcus* sp., *Leuconostoc* sp., *Pediococcus* sp., *Acetobacterium* sp., *Eubacterium* sp., *Heliobacterium* sp., *Heliospirillum* sp., *Sporomusa* sp., *Spiroplasma* sp., *Ureaplasma* sp., *Erysipelothrix* sp., *Corynebacterium* sp. *Enterococcus* sp., *Clostridium* sp., *Mycoplasma* sp., *Mycobacterium* sp., *Actinobacteria* sp., *Salmonella* sp., *Shigella* sp., *Moraxella* sp., *Helicobacter* sp, *Stenotrophomonas* sp., *Micrococcus* sp., *Neisseria* sp., *Bdellovibrio* sp., *Hemophilus* sp., *Klebsiella* sp., *Proteus mirabilis*, *Enterobacter cloacae*, *Serratia* sp., *Citrobacter* sp., *Proteus* sp., *Serratia* sp., *Yersinia* sp., *Acinetobacter* sp., *Actinobacillus* sp. *Bordetella* sp., *Brucella* sp., *Capnocytophaga* sp., *Cardiobacterium* sp., *Eikenella* sp., *Francisella* sp., *Haemophilus* sp., *Kingella* sp., *Pasteurella* sp., *Flavobacterium* sp. *Xanthomonas* sp., *Burkholderia* sp., *Aeromonas* sp., *Plesiomonas* sp., *Legionella* sp. and alpha-proteobacteria such as *Wolbachia* sp., cyanobacteria, spirochaetes, green sulfur and green non-sulfur bacteria, Gram-negative cocci, Gram negative bacilli which are fastidious, Enterobacteriaceae-glucose-fermenting gram-negative bacilli, Gram negative bacilli-non-glucose fermenters, Gram negative bacilli-glucose fermenting, oxidase positive.

Particularly useful bacterial host cells for protein expression include Gram negative bacteria, such as *Escherichia coli*, *Pseudomonas fluorescens*, *Pseudomonas haloplanctis*, *Pseudomonas putida* AC10, *Pseudomonas pseudoflava*, *Bartonella henselae*, *Pseudomonas syringae*, *Caulobacter crescentus*, *Zymomonas mobilis*, *Rhizobium meliloti*, *Myxococcus xanthus* and Gram positive bacteria such as *Bacillus subtilis*, *Corynebacterium*, *Streptococcus cremoris*, *Streptococcus lividans*, and *Streptomyces lividans*. *E. coli* is one of the most widely used expression hosts. Accordingly, the techniques for overexpression in *E. coli* are well developed and readily available to one of skill in the art. Further, *Pseudomonas fluorescens*, is commonly used for high level production of recombinant proteins (i.e. for the development bio-therapeutics and vaccines).

Particularly useful fungal host cells for protein expression include *Aspergillis oryzae*, *Aspergillis niger*, *Trichoderma reesei*, *Aspergillus nidulans*, *Fusarium graminearum*. Particularly useful yeast host cells for protein expression include *Candida albicans*, *Candida maltose*, *Hansenula polymorpha*, *Kluyveromyces fragilis*, *Kluyveromyces lactis*, *Pichia guillerimondii*, *Pichia pastoris*, *Saccharomyces cerevisiae*, *Schizosaccharomyces pombe*, and *Yarrowia lipolytica*.

Particularly useful mammalian host cells for protein expression include Chinese hamster ovary (CHO) cells, HeLa cells, baby hamster kidney (BHK) cells, monkey kidney cells (COS), human hepatocellular carcinoma cells (eg. Hep G2), human embryonic kidney cells, *Bos primigenius*, and *Mus musculus*. Additionally, the mammalian host cell may be an established, commercially-available cell line (e.g., American Type Culture Collection (ATCC), Manassas, Va.). The host cell may be an immortalized cell. Alternatively, the host cell may be a primary cell. "Primary cells" are cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines.

In another embodiment, the host cell may be in vivo; i.e., the cell may be disposed in a subject. Accordingly, a polypeptide of the invention is expressed from a host cell in the subject.

II. Methods

Another aspect of the present invention encompasses methods utilizing a composition described in Section I above.

In one embodiment, the invention encompasses a method for mediating asymmetric site-specific recombination in a nucleic acid. The method comprises contacting an isolated enzyme with a nucleic acid, wherein the isolated enzyme recognizes asymmetric sites on the nucleic acid and cleaves the asymmetric sites and wherein the asymmetric site-specific recombination is selected from the group consisting of inversion, excision, insertion and translocation. In a specific embodiment, the isolated enzyme is a tetrameric enzyme comprising subunit A and subunit B. In another specific embodiment, subunit A comprises the mutations: K25R, D29R, R32E, D33L, Q35R, E123L and R337E relative to SEQ ID NO:1 and subunit B comprises the mutations: E69D, R72K, L76E and E308R relative to SEQ ID NO:1.

In another embodiment, the invention encompasses a method for mediating asymmetric site-specific excision in a nucleic acid. The method comprises contacting an isolated enzyme with a nucleic acid, wherein the isolated enzyme recognizes asymmetric sites on the nucleic acid and cleaves the asymmetric sites thereby excising a portion of nucleic acid between the asymmetric site. In a specific embodiment, the isolated enzyme is a tetrameric enzyme comprising subunit A and subunit B. In another specific embodiment, subunit A comprises the mutations: K25R, D29R, R32E, D33L, Q35R, E123L and R337E relative to SEQ ID NO:1 and subunit B comprises the mutations: E69D, R72K, L76E and E308R relative to SEQ ID NO:1.

In still another embodiment, the invention encompasses a method for mediating asymmetric site-specific excision in a cell. The method comprises contacting an isolated enzyme or one or more enzyme constructs with a cell, wherein the isolated enzyme or polypeptide encoded by the enzyme construct recognizes asymmetric sites on the nucleic acid and cleaves the asymmetric sites thereby excising a portion of nucleic acid within the cell between the asymmetric site. In a specific embodiment, the isolated enzyme is a tetrameric enzyme comprising subunit A and subunit B. In another specific embodiment, the enzyme construct comprises a polynucleotide encoding at least one polypeptide, the polypeptide comprising subunit A, subunit B, or combinations thereof, wherein the isolated polynucleotide is encompassed in a recombinant vector that expresses the polypeptide. In still another specific embodiment, two enzyme constructs are contacted with a cell, wherein a first enzyme construct comprises a first polynucleotide encoding at least one polypeptide, the polypeptide comprising subunit A and a second enzyme construct comprises a second polynucleotide encoding at least one polypeptide, the polypeptide comprising subunit B. In yet another specific embodiment, subunit A comprises the mutations: K25R, D29R, R32E, D33L, Q35R, E123L and R337E relative to SEQ ID NO:1 and subunit B comprises the mutations: E69D, R72K, L76E and E308R relative to SEQ ID NO:1. In certain embodiments, the enzyme construct is encompassed in a recombinant vector selected from the group consisting of a naked plasmid, a plasmid within a liposome, a retroviral vector, an AAV vector, or a recombinant adenoviral vector.

In yet another embodiment, the invention encompasses a method for mediating recombination-mediated cassette exchange (RMCE) in a cell. The method comprises contacting an isolated enzyme or one or more enzyme constructs and an exogenous DNA molecule with a cellular endogenous genome, wherein the isolated enzyme or polypeptide encoded by the enzyme construct recognizes asymmetric sites on the cellular endogenous genome and wherein the RMCE occurs between the cellular endogenous genome and the exogenous DNA molecule such that the exogenous DNA molecule is integrated by recombination between the two asymmetric sites into a predetermined locus within the cellular genome. In a specific embodiment, the isolated enzyme is a tetrameric enzyme comprising subunit A and subunit B. In another specific embodiment, the enzyme construct comprises a polynucleotide encoding at least one polypeptide, the polypeptide comprising subunit A, subunit B, or combinations thereof, wherein the isolated polynucleotide is encompassed in a recombinant vector that expresses the polypeptide. In still another specific embodiment, two enzyme constructs are contacted with a cell, wherein a first enzyme construct comprises a first polynucleotide encoding at least one polypeptide, the polypeptide comprising subunit A and a second enzyme construct comprises a second polynucleotide encoding at least one polypeptide, the polypeptide comprising subunit B. In yet another specific embodiment, subunit A comprises the mutations: K25R, D29R, R32E, D33L, Q35R, E123L and R337E relative to SEQ ID NO:1 and subunit B comprises the mutations: E69D, R72K, L76E and E308R relative to SEQ ID NO:1. In certain embodiments, the enzyme construct is encompassed in a recombinant vector selected from the group consisting of a naked plasmid, a plasmid within a liposome, a retroviral vector, an AAV vector, or a recombinant adenoviral vector.

The present invention further provides methods for gene therapy comprising introducing into a subject a composition comprising an isolated enzyme or a composition comprising one or more enzyme constructs, wherein the isolated enzyme or polypeptide(s) encoded by the enzyme construct(s) facilitate site-specific recombination on asymmetric sites at a desired genomic locus. Alternatively, the method comprises introducing into a cell one or more enzyme constructs thereby modifying the cellular genome and further transplanting into a subject the genetically modified cell. The methods of the present invention provide for targeted recombination and are based on a priori determination of the insertion or excision genomic locus. Following identification of a desired locus, a recombinase is selected from a library of recombinases, for example altered recombination site specificities have been elicited in mutant Cre recombinases using directed evolution which can catalyze recombination at the desired locus. See for example, Buchholz and Stewart, *Nature biotechnology* 2001, 19, 1047-1052; Santoro and Schultz, *Proc Natl Acad Sci USA* 2002, 99, 4185-4190; and Sarkar et al., *Science* 2007, 316, 1912, all of which are hereby incorporated by reference in their entirety. The recombinase is then mutated to comprise the mutations described herein. For example, a first recombinase is selected which can catalyze recombination at a first desired locus and a second recombinase is selected which can catalyze recombination at a second desired locus. The first recombinase is then mutated to comprise the mutations of subunit A and the second recombinase is then mutated to comprise the mutations of subunit B. The reaction may be catalyzed when a heterotetrameric complex forms comprising two A subunits and two B subunits, wherein each of the four recombinases recognizes one half of a recombination site. Such methods are suitable for treating various diseases including diseases that require excision of an intervening sequence or diseases that could be treated by replacing a defective gene.

A subject of the invention may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In preferred embodiments, the subject is a mouse. In other preferred embodiments, the subject is a human.

In each of the above embodiments, a composition may further comprise an excipient. Non-limiting examples of excipients include antioxidants, binders, buffers, diluents (fillers), disintegrants, dyes, effervescent disintegration agents, preservatives (antioxidants), flavor-modifying agents, lubricants and glidants, dispersants, coloring agents, pH modifiers, chelating agents, preservatives (e.g., antibacterial agents, antifungal agents), release-controlling polymers, solvents, surfactants, and combinations of any of these agents.

Cells are contacted with the enzyme construct or isolated enzyme of the invention under effective conditions for a period of time sufficient to deliver an enzyme construct or isolated enzyme to a cell. In certain embodiments, the goal may be to deliver an enzyme construct to a cell of a subject. The subject's cell may be isolated, or the enzyme construct may be delivered to the cell in the subject. When the subject's cell is not isolated, the composition may be administered to the subject orally, parenterally, intraperitoneally, intravascularly, intrapulmonary, topically, intravitreally, or subretinally. The term parenteral as used herein includes subcutaneous, intravenous, intramuscular, intrathecal, or intrasternal injection, or infusion techniques.

III. Kits

Another aspect of the present invention encompasses kits comprising a composition described in Section I above.

In an embodiment, a kit comprises an isolated subunit A enzyme. In another embodiment, a kit comprises an isolated subunit B enzyme. In still another embodiment, a kit comprises an isolated subunit A enzyme and an isolated subunit B enzyme.

In another embodiment, a kit comprises an isolated enzyme comprising the mutations: K25R, D29R, R32E, D33L, Q35R, E123L and R337E relative to SEQ ID NO:1. In another embodiment, a kit comprises an isolated enzyme comprising the mutations: E69D, R72K, L76E and E308R relative to SEQ ID NO:1. In still another embodiment, a kit comprises a first isolated enzyme comprising the mutations: K25R, D29R, R32E, D33L, Q35R, E123L and R337E relative to SEQ ID NO:1 and a second isolated enzyme comprising the mutations: E69D, R72K, L76E and E308R relative to SEQ ID NO:1.

In a different embodiment, a kit comprises a polynucleotide sequence encoding at least one polypeptide, the polypeptide comprising subunit A, the polypeptide comprising subunit B or a combination thereof, wherein the polynucleotide is encompassed in a recombinant vector that expresses the polypeptide. In one embodiment, a kit comprises a polynucleotide sequence encoding at least one polypeptide, the polypeptide comprising subunit A, wherein the polynucleotide is encompassed in a recombinant vector that expresses the polypeptide. In another embodiment, the kit comprises a polynucleotide sequence encoding at least one polypeptide, the polypeptide comprising subunit B, wherein the polynucleotide is encompassed in a recombinant vector that expresses the polypeptide. In still another embodiment, the kit comprises a polynucleotide sequence encoding at least two polypeptides, a first polypeptide comprising subunit A and a second polypeptide comprising subunit B, wherein the polynucleotide is encompassed in a recombinant vector that expresses the polypeptide. In still another embodiment, a kit may comprise a cell comprising a polynucleotide sequence as described in the foregoing embodiments.

In another different embodiment, a kit comprises a polynucleotide sequence encoding at least one polypeptide, the polypeptide comprising the mutations: K25R, D29R, R32E, D33L, Q35R, E123L and R337E relative to SEQ ID NO:1, the polypeptide comprising the mutations: E69D, R72K, L76E and E308R relative to SEQ ID NO:1 or a combination thereof, wherein the polynucleotide is encompassed in a recombinant vector that expresses the polypeptide. In one embodiment, a kit comprises a polynucleotide sequence encoding at least one polypeptide, the polypeptide comprising the mutations: K25R, D29R, R32E, D33L, Q35R, E123L and R337E relative to SEQ ID NO:1, wherein the polynucleotide is encompassed in a recombinant vector that expresses the polypeptide. In another embodiment, the kit comprises a polynucleotide sequence encoding at least one polypeptide, the polypeptide comprising the mutations: E69D, R72K, L76E and E308R relative to SEQ ID NO:1, wherein the polynucleotide is encompassed in a recombinant vector that expresses the polypeptide. In still another embodiment, the kit comprises a polynucleotide sequence encoding at least two polypeptides, a first polypeptide comprising the mutations: K25R, D29R, R32E, D33L, Q35R, E123L and R337E relative to SEQ ID NO:1 and a second polypeptide comprising the mutations: E69D, R72K, L76E and E308R relative to SEQ ID NO:1, wherein the polynucleotide is encompassed in a recombinant vector that expresses the polypeptide. In still another embodiment, a kit may comprise a cell comprising a polynucleotide sequence as described in the foregoing embodiments.

In certain embodiments, a kit further comprises an exogenous DNA molecule for recombination-mediated cassette exchange (RMCE). A kit may further comprise instructions for use and/or buffers.

TABLE A

Sequences.

| SEQ ID NO: | Name | Sequence |
|---|---|---|
| 1 | WT Cre recombinase | MSNLLTVHQN LPALPVDATS DEVRKNLMDM FRDRQAFSEH TWKMLLSVCR SWAAWCKLNN RKWFPAEPED VRDYLLYLQA RGLAVKTIQQ HLGQLNMLHR RSGLPRPSDS NAVSLVMRRI RKENVDAGER AKQALAFERT DFDQVRSLME NSDRCQDIRN LAFLGIAYNT LLRIAEIARI RVKDISRTDG GRMLIHIGRT KTLVSTAGVE KALSLGVTKL VERWISVSGV ADDPNNYLFC RVRKNGVAAP SATSQLSTRA LEGIFEATHR LIYGAKDDSG QRYLAWSGHS ARVGAARDMA RAGVSIPEIM QAGGWTNVNI VMNYIRNLDS ETGAMVRLLE DGD |
| 2 | Cre recombinase-Subunit A | MSNLLTVHQN LPALPVDATS DEVRRNLMRM FELRRAFSEH TWKMLLSVCR SWAAWCKLNN RKWFPAEPED VRDYLLYLQA RGLAVKTIQQ HLGQLNMLHR RSGLPRPSDS NAVSLVMRRI RKLNVDAGER AKQALAFERT DFDQVRSLME NSDRCQDIRN LAFLGIAYNT LLRIAEIARI RVKDISRTDG GRMLIHIGRT KTLVSTAGVE KALSLGVTKL VERWISVSGV ADDPNNYLFC RVRKNGVAAP SATSQLSTRA LEGIFEATHR LIYGAKDDSG QRYLAWSGHS ARVGAARDMA RAGVSIPEIM QAGGWTNVNI VMNYIRNLDS ETGAMVELLE DGD |

TABLE A-continued

Sequences.

| SEQ ID NO: | Name | Sequence |
|---|---|---|
| 3 | Cre recombinase-Subunit B | MSNLLTVHQN LPALPVDATS DEVRKNLMDM FRDRQAFSEH TWKMLLSVCR SWAAWCKLNN RKWFPAEPDD VKDYLEYLQA RGLAVKTIQQ HLGQLNMLHR RSGLPRPSDS NAVSLVMRRI RKENVDAGER AKQALAFERT DFDQVRSLME NSDRCQDIRN LAFLGIAYNT LLRIAEIARI RVKDISRTDG GRMLIHIGRT KTLVSTAGVE KALSLGVTKL VERWISVSGV ADDPNNYLFC RVRKNGVAAP SATSQLSTRA LEGIFEATHR LIYGAKDDSG QRYLAWSGHS ARVGAARDMA RAGVSIPRIM QAGGWTNVNI VMNYIRNLDS ETGAMVRLLE DGD |
| 4 | Natural LoxP site | ATAACTTCGTATAGCATACATTATACGAAGTTAT |
| 5 | M7 site | ATAACTCTATATAGCATACATTATATAGAGTTAT |
| 6 | LoxP-M7 site | ATAACTTCGTATAGCATACATTATATAGAGTTAT |

Definitions

The term "polynucleotide" is intended to encompass a singular nucleic acid as well as plural nucleic acids, and refers to an isolated nucleic acid molecule or construct, e.g., messenger RNA (mRNA), cDNA, or vector DNA. A polynucleotide may comprise a conventional phosphodiester bond or a non-conventional bond (e.g., an amide bond, such as found in peptide nucleic acids (PNA)). The term "nucleic acid" refers to any one or more nucleic acid segments, e.g., DNA or RNA fragments, present in a polynucleotide. By "isolated" nucleic acid or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. Isolated RNA molecules include in vivo or in vitro RNA transcripts of polynucleotides of the present invention. Isolated polynucleotides or nucleic acids according to the present invention further include such molecules produced synthetically. In addition, polynucleotide or a nucleic acid may be or may include a regulatory element such as a promoter, ribosome binding site, or a transcription terminator.

As used herein, a "coding region" is a portion of nucleic acid which consists of codons translated into amino acids. Although a "stop codon" (TAG, TGA, or TAA) is not translated into an amino acid, it may be considered to be part of a coding region, but any flanking sequences, for example promoters, ribosome binding sites, transcriptional terminators, introns, and the like, are not part of a coding region. Two or more coding regions of the present invention can be present in a single polynucleotide construct, e.g., on a single vector, or in separate polynucleotide constructs, e.g., on separate (different) vectors. Furthermore, any vector may contain a single coding region, or may comprise two or more coding regions, e.g., a single vector may separately encode subunit A and subunit B or a single vector may separately encode subunit A and a second subunit A. In addition, a vector, polynucleotide, or nucleic acid of the invention may encode heterologous coding regions, either fused or unfused to a nucleic acid encoding a polypeptide. Heterologous coding regions include without limitation specialized elements or motifs, such as a signal peptide or a heterologous functional domain.

In certain embodiments, the polynucleotide or nucleic acid is DNA. In the case of DNA, a polynucleotide comprising a nucleic acid which encodes a polypeptide normally may include a promoter and/or other transcription or translation control elements operably associated with one or more coding regions. An operable association is when a coding region for a gene product, e.g., a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" or "operably linked" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription. Suitable promoters and other transcription control regions are disclosed herein.

A variety of transcription control regions are known to those skilled in the art. The term "control regions" refers to DNA sequences necessary for the expression of an operably linked coding sequence in a particular host organism. The control regions that are suitable for prokaryotes, for example, include a promoter, optionally an operator sequence, and a ribosome binding site. Eukaryotic cells are known to utilize promoters, polyadenylation signals, and enhancers. These include, without limitation, transcription control regions which function in vertebrate cells, such as, but not limited to, promoter and enhancer segments from cytomegaloviruses (the immediate early promoter, in conjunction with intron-A), simian virus 40 (the early promoter), and retroviruses (such as Rous sarcoma virus). Other transcription control regions include those derived from vertebrate genes such as actin, heat shock protein, bovine growth hormone and rabbit β-globin, as well as other sequences capable of controlling gene expression in eukaryotic cells. Additional suitable transcription control regions include tissue-specific promoters and enhancers as well as lymphokine-inducible promoters (e.g., promoters inducible by interferons or interleukins).

Similarly, a variety of translation control elements are known to those of ordinary skill in the art. These include, but are not limited to ribosome binding sites, translation initiation and termination codons, and elements derived from picornaviruses (particularly an internal ribosome entry site, or RES, also referred to as a CITE sequence).

In other embodiments, a polynucleotide of the present invention is RNA, for example, in the form of messenger RNA (mRNA).

Polynucleotide and nucleic acid coding regions of the present invention may be associated with additional coding regions which encode secretory or signal peptides, which direct the secretion of a polypeptide encoded by a polynucleotide of the present invention. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the complete or "full-length" polypeptide to produce a secreted or "mature" form of the polypeptide. In certain embodiments, the native signal peptide, e.g., a Cre recombinase signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

A "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms.

The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

A polypeptide of the invention may be of a size of about 3 or more, 5 or more, 10 or more, 20 or more, 25 or more, 50 or more, 75 or more, 100 or more, 200 or more, 500 or more, 1,000 or more, or 2,000 or more amino acids. Polypeptides may have a defined three-dimensional structure, although they do not necessarily have such structure. Polypeptides with a defined three-dimensional structure are referred to as folded, and polypeptides which do not possess a defined three-dimensional structure, but rather can adopt a large number of different conformations, and are referred to as unfolded. As used herein, the term glycoprotein refers to a protein coupled to at least one carbohydrate moiety that is attached to the protein via an oxygen-containing or a nitrogen-containing side chain of an amino acid residue, e.g., a serine residue or an asparagine residue.

"Isolated," when used to describe the various polypeptides disclosed herein, means a polypeptide has been identified and separated and/or recovered from a cell or cell culture from which it was expressed. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

An "isolated" nucleic acid encoding a polypeptide or other polypeptide-encoding nucleic acid is a nucleic acid molecule that is identified and separated from at least one contaminant nucleic acid molecule with which it is ordinarily associated in the natural source of the polypeptide-encoding nucleic acid. An isolated polypeptide-encoding nucleic acid molecule is other than in the form or setting in which it is found in nature. Isolated polypeptide-encoding nucleic acid molecules therefore are distinguished from the specific polypeptide-encoding nucleic acid molecule as it exists in natural cells. However, an isolated polypeptide-encoding nucleic acid molecule includes polypeptide-encoding nucleic acid molecules contained in cells that ordinarily express the polypeptide where, for example, the nucleic acid molecule is in a chromosomal location different from that of natural cells.

An "isolated" cell is a cell isolated from a native source.

EXAMPLES

The following examples are included to demonstrate preferred embodiments of the invention. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction to the Examples

Cre recombinase forms a tetrameric complex that splices DNA molecules containing the 34-bp recombination target (RT) site loxP {Sternberg and Hamilton, 1981, J Mol Biol, 150, 467-86}, recombining two DNA molecules in trans to accomplish an insertion or translocation event, or in cis to achieve either gene excision or inversion, depending on the relative orientation of the loxP sites (FIG. 1). Cre recombinase has been used to generate conditional gene knockouts, where a gene of interest is flanked by loxP sites ('floxed') {Gu et al., 1993, Cell, 73, 1155-64}. Expression of Cre recombinase under the control of promoters that are specific for particular tissues or developmental stages abrogates gene function by physical excision from the genome. The utility of this system depends on the functional autonomy of Cre recombinase: the enzyme requires no other factors to splice DNA, and is capable of modifying genomes in non-replicating cells, where the efficacy of gene conversion via double-strand break (DSB) induced homologous recombination is expected to be low {Saleh-Gohari and Helleday, 2004, Nucleic Acids Res, 32, 3683-8; Rothkamm et al., 2003, Mol Cell Biol, 23, 5706-15}.

Another application for Cre recombinase is recombination-mediated cassette exchange (RMCE) {Bouhassira et al., 1997, Blood, 90, 3332-3344}, also known as double-reciprocal crossover {Schlake and Bode, 1994, Biochemistry, 33, 12746-12751; Seibler and Bode, 1997, Biochemistry, 36, 1740-1747} or double-lox replacement {Bethke and Sauer, 1997, Nucleic Acids Res, 25, 2828-34; Soukharev et al., 1999, Nucleic Acids Res, 27, e21}. In this approach, (reviewed in ref. {Turan et al., 2013, Gene, 515, 1-27}) recombination between DNA molecules that share two neighboring heterologous RT sites accomplishes the exchange of the bounded genetic interval (the cassette) between the sites (FIG. 1C). This has been demonstrated using both Flp and Cre recombinase with heterologous RT variants {Bethke and Sauer, 1997, Nucleic Acids Res, 25, 2828-34; Bouhassira et al., 1997, Blood, 90, 3332-3344}, as well as simultaneously with Cre and the Flp recombinases {Anderson et al., 2012, Nucleic Acids Res, 40, e62}. Although RMCE has so far only been demonstrated with wild-type recombinase proteins and RT sites, the approach has many attractive features as a tool for genome engineering. First, it has a higher efficiency for gene conversion than does Cre-mediated insertion, as it does not require survival of insertional events that are susceptible to reversal by excision {Bethke and Sauer, 1997, Nucleic Acids Res, 25, 2828-34}. Second, the cassettes that are exchanged are precisely demarcated, yielding truly 'scarless' genomic surgery. Third, the process requires less Cre protein than recombinational insertion, resulting in less cytotoxicity {Bethke and Sauer, 1997, Nucleic Acids Res, 25, 2828=34}. Finally, the autonomy of Cre as a recombinase suggests that RMCE could prove to be effective in terminally differentiated cells, in contrast to strategies for gene conversion that rely upon homology directed repair.

One impediment to broader use of Cre recombinase is the inflexibility of the binding site specificity. In contrast to DNA binding proteins whose specificity derives from the assembly of small recognition modules such as zinc finger or TAL effector domains, Cre recombinase interacts with DNA through large interfaces that defy a modular decomposition. Nevertheless, altered RT specificities have been elicited in mutant Cre recombinases using directed evolution {Buchholz and Stewart, 2001, Nature biotechnology, 19, 1047-1052; Santoro and Schultz, 2002, Proc Natl Acad Sci USA, 99, 4185-4190; Sarkar et al., 2007, Science, 316, 1912}.

The quaternary structure of the Cre complex creates a second challenge for engineering novel RT specificities. The four-fold symmetry in the functional protein complex imposes a pseudo-palindromic symmetry upon the RT site. The loxP site consists of two 13 bp palindromic half-sites separated by an asymmetric 8 bp spacer that gives loxP its direction. The utility of targeting Cre mutants to altered RT sites is severely compromised if only pseudo-palindromic sites may be considered. This limitation has been addressed by using directed evolution to generate mutant homotetrameric complexes that can operate on asymmetric sites {Bolusani et al., 2006, Nucleic acids research, 34, 5259; Sarkar et al., 2007, Science, 316, 1912}. However, requiring a single Cre mutant to operate on two different half-sites is likely to result in promiscuous enzymes. Separate Cre mutants with specificities towards the two half-sites of an asymmetric RT site may be able to recombine these sites, but the lack of control over assembly of the complex allows for any combination of these half-sites as potential sites for recombination {Saraf-Levy et al., 2006, Bioorganic & medicinal chemistry, 14, 3081-3089}. Some of these combinations will be undesired, generating off-target recombination events and exacerbating the cytotoxicity of Cre recombinase {Loonstra et al., 2001, Proc Natl Acad Sci USA, 98, 9209-14}.

A similar technical challenge has been overcome in the design of zinc finger nucleases (ZFNs). ZFNs are DSB agents that achieve their sequence specificity by concatenating multiple zinc finger modules, each of which recognizes 3-4 base pairs. The cleavage activity is provided by the dimeric FokI nuclease. FokI monomers are genetically fused to zinc finger arrays, and two such constructs that converge upon a DNA site reconstitute a functional nuclease dimer, inducing a DSB. The development of obligate heterodimer FokI mutants has increased target specificity and reduced cytotoxicity in this system {Szczepek et al., 2007, Nat Biotechnol, 25, 786-93}. Under this approach, the ZFNs that co-locate on desired cleavage sites must contribute two distinct FokI monomers; misassembly of two copies of the same ZFN at an off-target site cannot reconstitute a functional nuclease. Constructing a functional Cre complex from distinguishable and separately mutatable monomers is an attractive strategy for enhancing the specificity of RT site recognition. An earlier effort to generate heterotetramer Cre mutants succeeded in forming a novel functional interface, but one of the two mutants retained significant activity as a homotetramer {Gelato et al., 2008, J Mol Biol, 378, 653-665}.

Here we describe the engineering of Cre mutants that are inactive in isolation, but are functional as a (ABAB) heterotetramer when both mutants are present. We use a combination of computational and rational design to select mutations that are predicted to form a novel interface between Cre monomers that is functional, but whose halves are incompatible with their wild-type counterparts. We show that the negative engineering goal (incompatibility with wild-type) is more difficult to achieve than the positive goal (full functionality), requiring three iterations of mutation. The obligate heterotetrameric assembly of the pair of mutants is demonstrated in vitro and in vivo, notably in mammalian cells. We hope that the availability of these mutants enables the specific and reliable targeting of Cre to asymmetric RT sites.

Example 1. Computational Redesign of a Non-Native but Functional Protein-Protein Interface Between Cre Recombinase Monomers We desired an engineered protein interface between Cre recombinase monomers that could form a functional complex, yet be incompatible with the wild-type interface. The two sides of such an interface could then be mixed with the other sides of the wild-type interface to yield two distinct Cre mutants. These mutants, by virtue of possessing incompatible interfaces, could not form functional homotetrameric complexes, but could be combined to form a functional heterotetramer (FIG. 1D). We selected the 2.2 Å crystal structure of a Cre-loxP Holliday junction (PDB code: 1 KBU) {Martin et al., 2002, J Mol Biol, 319, 107-27} as our template for computational design. We then selected the largest monomer-monomer interface patch for redesign, focusing on residues that did not participate in any contacts with DNA (cyan oval on left side of FIG. 1A). We used the Rosetta molecular modeling program to redesign five residues on each side of the interface (see Methods for the Examples), although in some cases the wild-type amino acid was retained by the design calculation.

We tested the redesigned interface by generating pairs of Cre mutants such that each mutant possesses one side of the interface, with the other side fixed as wild-type. We assayed members of each pair for recombinase activity in vitro both individually and in combination (FIG. 2). While the combined pair of redesigned mutants was active (Cre-A1+Cre-B1 in FIG. 2B; see Table 1 for mutations), one of the mutants (Cre-A1) was active individually, indicating that this hybrid redesign/wild-type interface was functionally compatible, in violation of our negative engineering goal (FIG. 1D)

TABLE 1

Cre Mutants

| Cre mutant | Mutations |
|---|---|
| Cre-A1 | K25R, D29R, R32E, D33L, Q35R |
| Cre-B1 | E69D, R72K, L76E |
| Cre-A2 | Cre-A1 + R337E |
| Cre-B2 | Cre-B1 + E308R |
| Cre-A3 | Cre-A2 + E123L |
| Cre-B3 | Cre-B2 + E123L |

Figure 2A:
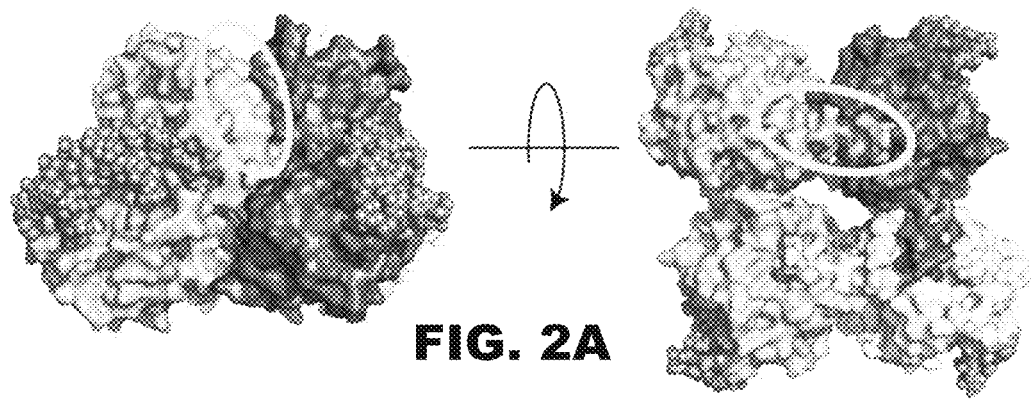
FIG. 2A, FIG. 2B, FIG. 2C, FIG. 2D and FIG. 2E depict images showing the mutated positions in the monomer-monomer interface.
Figure 2B:
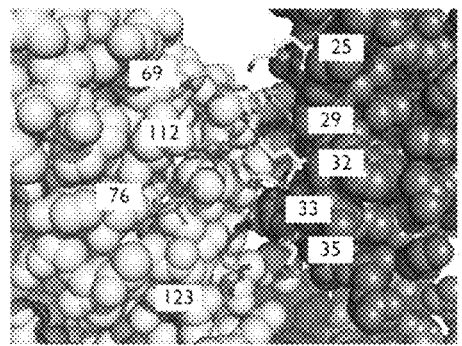
Figure 2C:
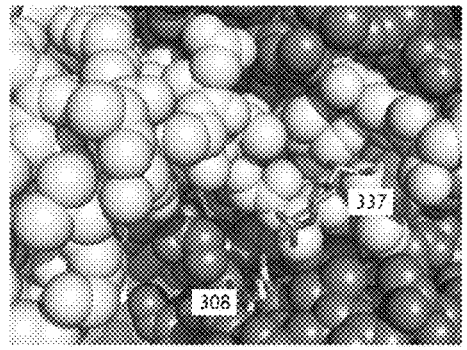
Figure 2D:
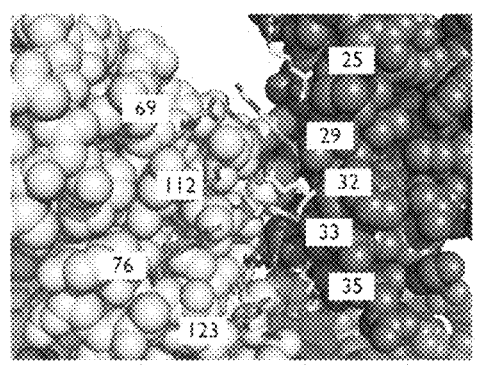
Figure 2E:
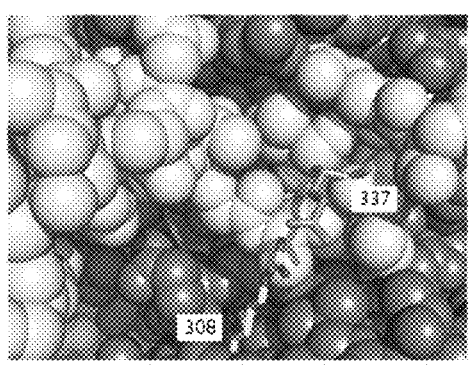

Example 2. Iterative Rounds of Rational Design Enhance the Formation of (ABAB) Complexes We attempted to find another region of contact between monomers in the Cre complex that we could mutate in an attempt to further destabilize homotetrameric Cre-A1 complexes. Visual inspection of the Cre crystal structure revealed a salt bridge between Glu308 and Arg337 (FIG. 2C) that we hypothesized could be inverted to obtain additional specificity for the heterotetramic complex (FIG. 2E). We therefore further mutated Cre-A1 (adding R337E) to yield Cre-A2, and mutated Cre-B1 (adding E308R) to yield Cre-B2. Thus, homotetrameric complexes of Cre-A2 would place two glutamate residues at 308 and 337 in close proximity, and Cre-B2 would likewise pair two arginine residues, yielding unfavorable electrostatic repulsion in either case. Our in vitro recombinase assay showed that the Cre-A2+Cre-B2 combination exhibited strong recombinase activity. However, while its activity is reduced relative to Cre-A1, the Cre-A2 monomer was still capable of forming a functional homotetrameric complex (FIG. 2B).

We selected a polar interaction between monomers as the final site for mutagenesis. We hypothesized that a replacement interaction consisting of hydrophobic residues would be incompatible with the pre-existing polar interaction. Structural modeling suggested that the mutation E123L and Q35L could create a tight packing interaction between leucine residues across the monomer-monomer interface, but that interfaces combining a polar residue from the wild-type interface with either leucine from the engineered interface would be energetically unfavorable.

In vitro assays indicated that the E123L mutation did indeed penalize formation of functional homotetrameric complexes, but that the Q35L mutation unexpectedly facilitated homotetramer formation in the previously inactive B2 mutant (data not shown). Consequently, we applied the E123L mutation to Cre-A2 to create Cre-A3. This mutation successfully disrupted formation of Cre-A2 homotetramers while preserving activity in the Cre-A3+Cre-B2 heterotetramer (FIG. 2B). The improvement in specificity appears to come from selective destabilization of the Cre-A3 homotetramer with limited destabilization of the heterotetramer.

Figures 6A, 6B:
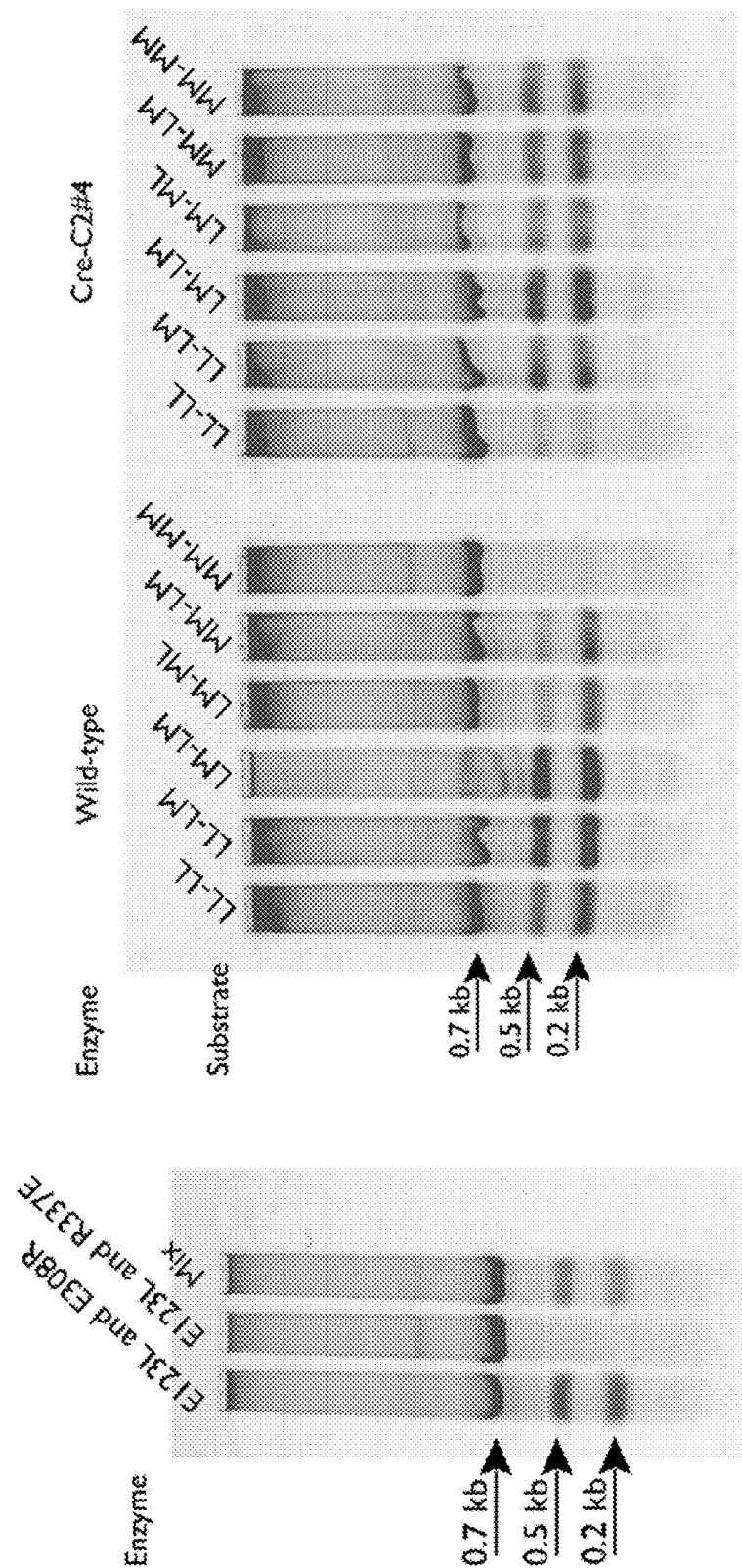
FIG. 6A and FIG. 6B depict gels showing an in vitro recombination assay of Cre mutants.

To test whether our round 1 mutations are essential to enforce heterotetramer formation, we generated Cre mutants with only round 2 and round 3 mutations. The salt-bridge swap from round 2 alone yields two Cre mutants with reduced but clear activity (data not shown). We combined round 2 and round 3 mutations to create Cre-E123L-E308R and Cre-E123LE-R337E. In vitro assays indicated that these mutants do not form an obligate heterotetrameric pair (FIG. 6A). We conclude that the combined effects of mutations from all three rounds are necessary to achieve our design goal.

Example 3. Heterotetrameric Mutations can be Combined with DNA Specificity Altering Mutations to Enhance Target Site Specificity We hypothesized that the ability to control the assembly of functional Cre complexes would lead to higher fidelity recognition of asymmetric RT sites if used in combination with recombinases with different DNA specificities. Directed evolution has already been exploited to generate mutants of Cre recombinase that can utilize altered RT sites. A mutant (termed Cre-C2#4) with five amino acid mutations relative to wild-type has been shown to recombine an alternate RT site termed M7 {Santoro and Schultz, 2002, Proc Natl Acad Sci USA, 99, 4185-4190}. The monomer-monomer interface mutations from Cre-A3 and Cre-B2 were applied to the Cre-C2#4 mutant. If the proteins with different DNA specificities exhibit the expected ABAB heterotetrameric pattern assembly, they should only recombine DNA half-sites with a specific spatial arrangement, yielding enhanced target specificity.

Figure 3A:
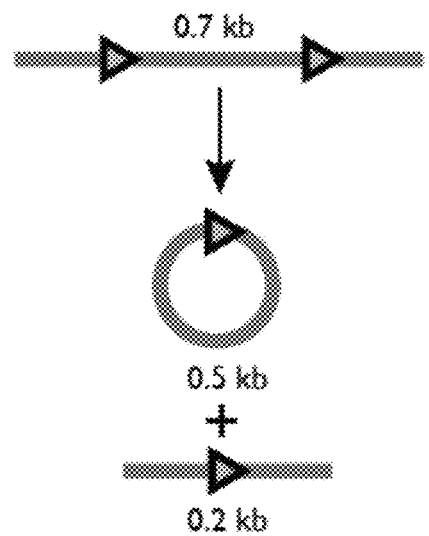
FIG. 3A, FIG. 3B, FIG. 3C and FIG. 3D depict schematics and gels showing and in vitro recombination assay of Cre mutants.
Figure 3B:
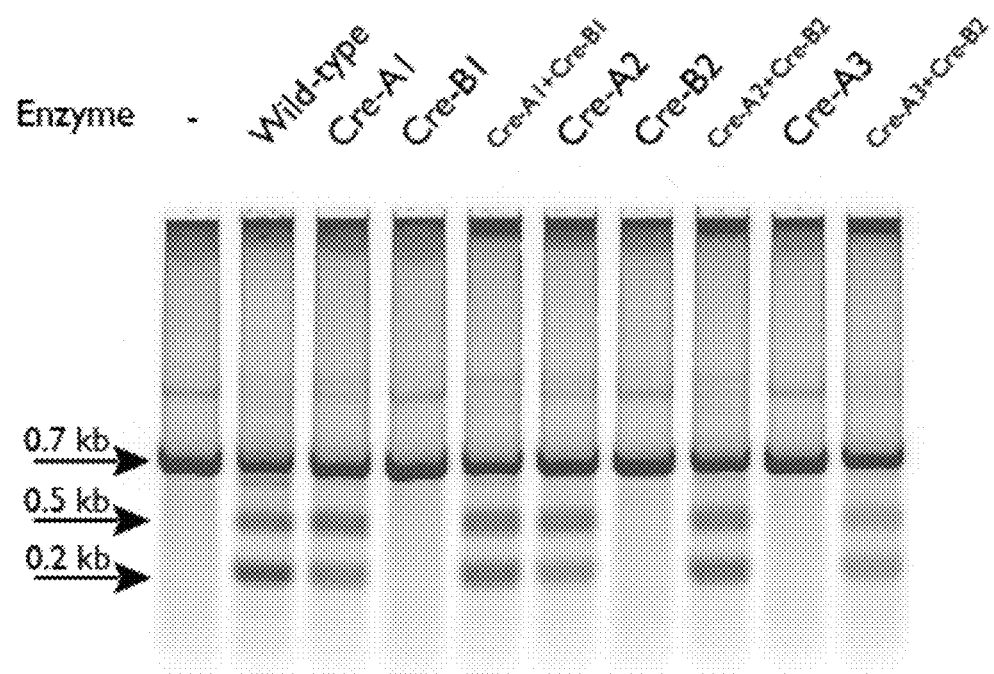
Figure 3C:
Figure 3C:
Figure 3C:
Figure 3C:
Figure 3C:
Figure 3C:

To this end, we designed direct repeats of six loxP/M7 hybrid RT sites as a rigorous test of specificity (FIG. 3C). We expect that a mixture of wild-type Cre and Cre-C2#4 (both of which lack our obligate heterotetrameric mutations) could recombine all of the six RT sites, as the individual monomers can combine in a manner dictated by the sequences of the RT half-sites. In contrast, a combination of the designed Cre-A3-C2#4 and Cre-B2 recombinases, or similarly the Cre-A3 and Cre-B2-C2#4 recombinase, would specifically recombine the LM-LM site, but not the other five RT sites (FIG. 3C). If so, the heterotetrameric Cre mutants will have less off-target activity when used for genome editing.

Figure 3D:
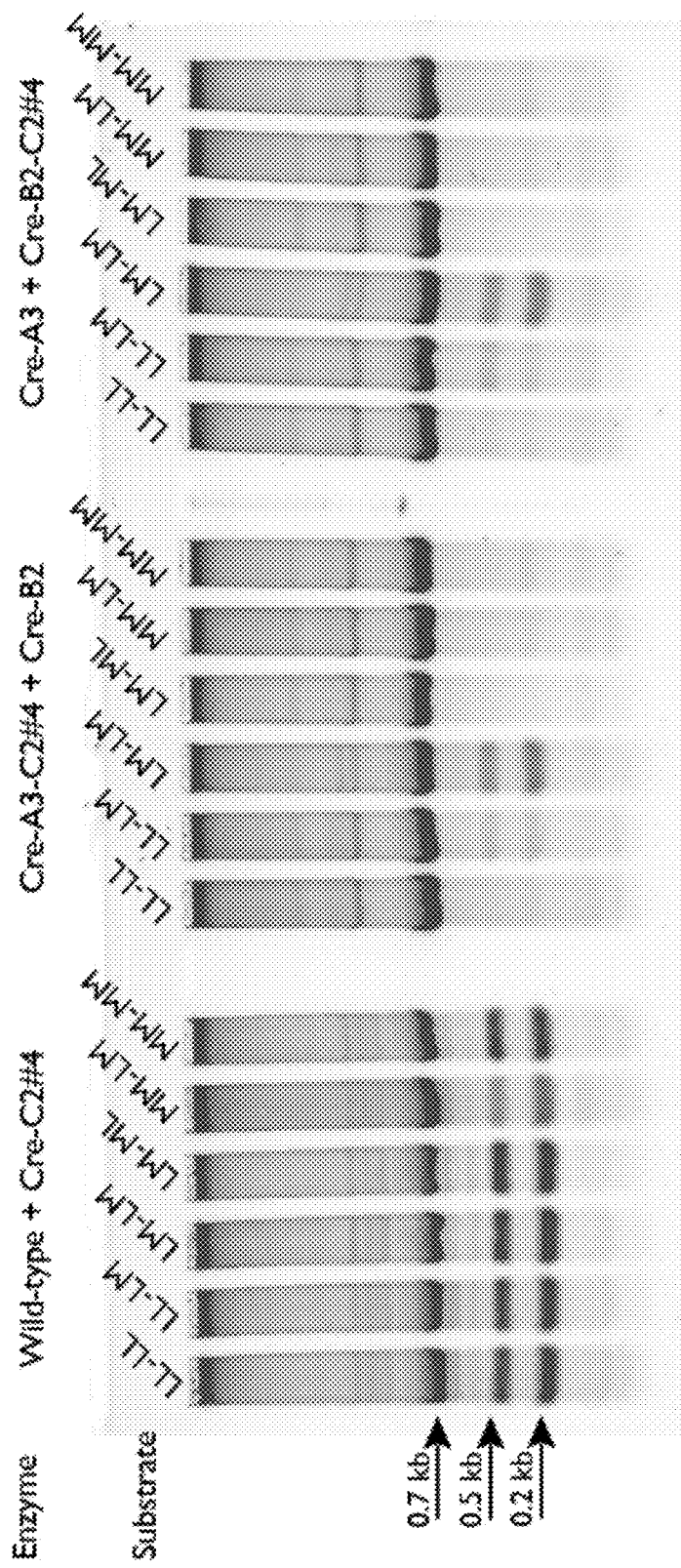

In vitro assays confirmed that the heterotetrameric Cre is more specific in recombining different arrangement of loxP/M7 sites (FIG. 3D). Cre-C2#4 is slightly promiscuous, and can recombine loxP sites when incubated with DNA substrate for a long period of time ({Santoro and Schultz, 2002, Proc Natl Acad Sci USA, 99, 4185-4190}), FIG. 6B). The observed partial activity of the two designed pairs on LL-ML site (lane 2 in the middle and right gels of FIG. 3D) is most likely the result of promiscuity of Cre-C2#4's DNA specificity. It is also interesting to note that, because the four Cre monomers work cooperatively to recombine the DNA target, wild-type Cre and Cre-C2#4 homotetramers recombined most of the loxP/M7 hybrid sites on their own ({Sheren et al., 2007, Nucleic Acids Res, 35, 5464-73}, FIG. 6B). The specificity shown here by the two designed pairs provides strong evidence that our mutant recombinases indeed form an ABAB heterotetrameric complex.

Example 4. Obligate Heterotetramer Formation is Preserved in Mammalian Cells

Figure 4A:
FIG. 4A and FIG. 4B depict a schematic and graph showing Cre mutant pair recapitulates requirement for heterotetramer formation in mouse ES cell cultures.
Figure 4B:
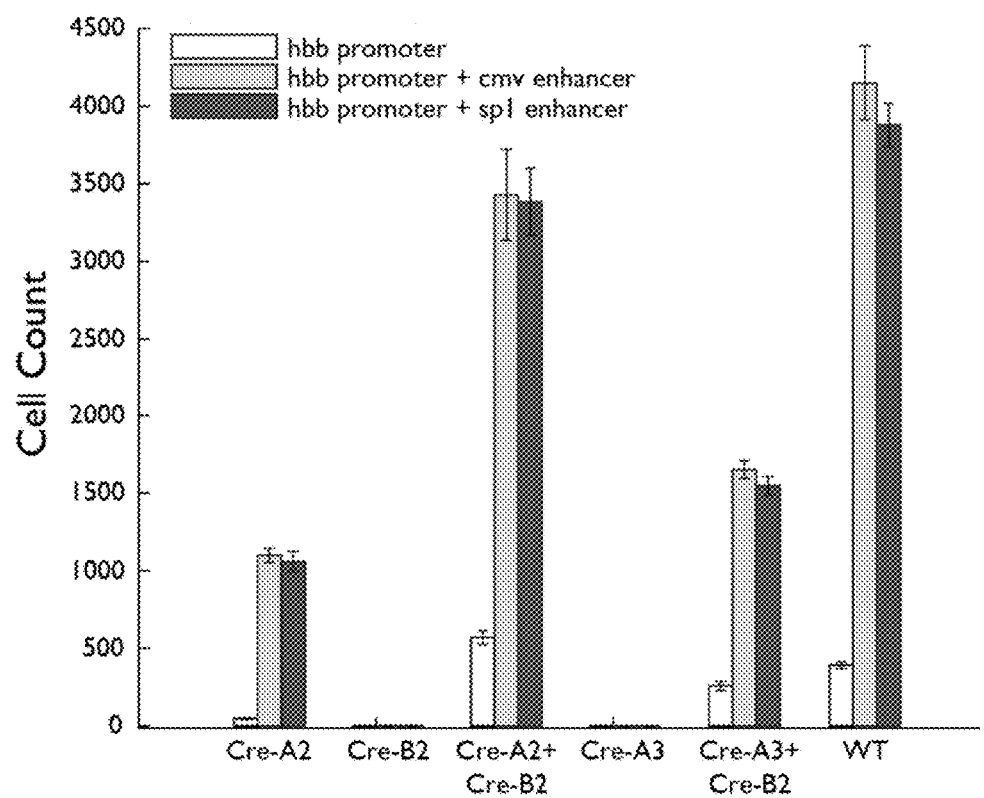

We envision RMCE in mammalian cells as the target application for our heterotetramer-forming Cre mutants. We employed two reporter systems to determine whether the engineered proteins satisfy our design goals in mammalian cells. First, we assayed the recombinase activity of the Cre mutants in a mouse ES cell reporter line by flow cytometry. We inserted a gene for the tandem dimer tomato (tdTomato) fluorescent protein downstream of a floxed stop codon at the rosa26 locus (FIG. 4A). Constructs encoding genes for the Cre mutants driven by the haemoglobin beta (HBB) minimal gene promoter, either alone or in combination with one of two enhancers (see Methods for the Examples), were transfected into the reporter line, and the cells expressing tdTomato were quantified by flow cytometry (FIG. 4B, Table 2).

TABLE 2

Cell sorting data from mouse ES cells.

| Cre variant(s) | promoter | Replicate | | |
|---|---|---|---|---|
| | | $1^{st}$ | $2^{nd}$ | $3^{rd}$ |
| | | Total # of cells sorted | | |
| | | 7000 | 7000 | 7000 |
| Cre-A1 | hbb | 414 | 378 | 391 |
| | hbb + cmv | 3852 | 3528 | 3687 |
| | hbb + sp1 | 3750 | 3419 | 3501 |
| Cre-B1 | hbb | 97 | 102 | 85 |
| | hbb + cmv | 1237 | 1258 | 1120 |
| | hbb + sp1 | 1150 | 1080 | 1202 |
| A1 + B1 | hbb | 1117 | 1212 | 1324 |
| | hbb + cmv | 5866 | 6029 | 6358 |
| | hbb + sp1 | 5702 | 6121 | 5987 |
| Cre-A2 | hbb | 47 | 52 | 41 |
| | hbb + cmv | 1127 | 1116 | 1052 |
| | hbb + sp1 | 1053 | 1002 | 1119 |
| Cre-B2 | hbb | 0 | 0 | 1 |
| | hbb + cmv | 2 | 2 | 4 |
| | hbb + sp1 | 2 | 1 | 3 |
| A2 + B2 | hbb | 573 | 528 | 607 |
| | hbb + cmv | 3180 | 3409 | 3698 |
| | hbb + sp1 | 3221 | 3336 | 3593 |
| Cre-A3 | hbb | 0 | 0 | 1 |
| | hbb + cmv | 0 | 1 | 1 |
| | hbb + sp1 | 1 | 0 | 0 |
| Cre-B3 | hbb | 0 | 0 | 0 |
| | hbb + cmv | 0 | 0 | 1 |
| | hbb + sp1 | 1 | 0 | 0 |
| A3 + B3 | hbb | 0 | 1 | 0 |
| | hbb + cmv | 1 | 2 | 1 |
| | hbb + sp1 | 1 | 1 | 2 |
| A3 + B2 | hbb | 256 | 233 | 284 |
| | hbb + cmv | 1598 | 1652 | 1701 |
| | hbb + sp1 | 1503 | 1527 | 1606 |
| WT | hbb | 372 | 391 | 408 |
| | hbb + cmv | 3914 | 4223 | 4312 |
| | hbb + sp1 | 3815 | 3799 | 4021 |

Plasmids with the hbb minimal promoter, cmv and sp1 enhancer driving different cre variants were co-transfected into Ai14 mouse embryonic stem (ES) cells containing a reporter cassette with RFP preceded by a floxed stop codon. The same total amount of DNA was used for all transfections, and 3 independent transfections were performed for each Cre variant. The number of RFP positive cells was measured by flow cytometry.

Similar to the results in bacterial cells, we observed the Cre-A2+Cre-B2 combination to be functional, while the Cre-A2 mutant retains significant activity as a homotetramer. Combining Cre-A3 with Cre-B2 yielded a suitable obligate heterotetrameric pair, retaining roughly 40% of wild type Cre activity. Neither the Cre-A3 nor the Cre-B2 mutants exhibited appreciable activity alone.

Figure 5A:
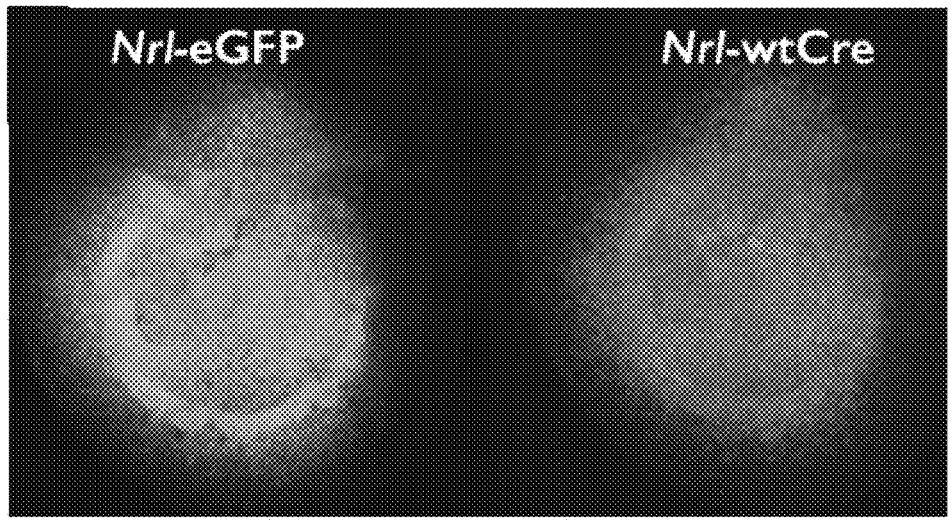
FIG. 5A, FIG. 5B, FIG. 5C, FIG. 5D and FIG. 5E depict images and a graph showing engineered Cre mutants retain preference for heterotetrameric complex in mouse retinal cells. Dissected newborn mouse retinas (with lens in place) were electroporated with constructs encoding: (1) Nrl-eGFP as a control for electroporation efficiency, (2) a reporter construct for Cre activity comprised of DsRed preceded by a floxed stop codon, and (3) a gene encoding either wild-type (FIG. 5A) or engineered Cre (FIG. 5B, FIG. 5C, FIG. 5D) under control of the Nrl promoter. The left side of each panel shows the fluorescence from the green channel, which indicates cells that were successfully electroporated. Fluorescence from the red channel results from removal of the floxed stop codon, indicating Cre activity. The lens shows some autofluorescence which is apparent as a central circular region of red fluorescence in B, C, and D.
Figure 5B:
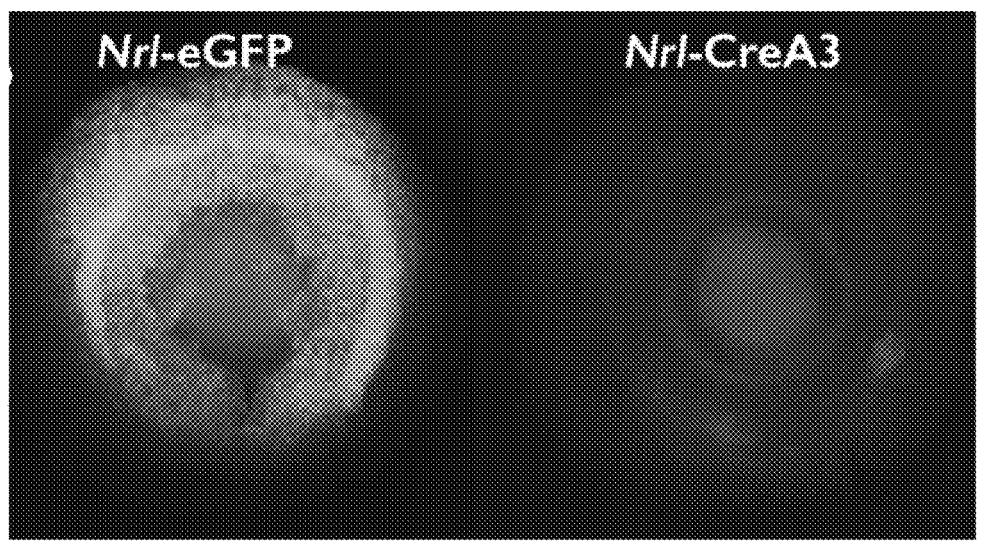
Figure 5C:
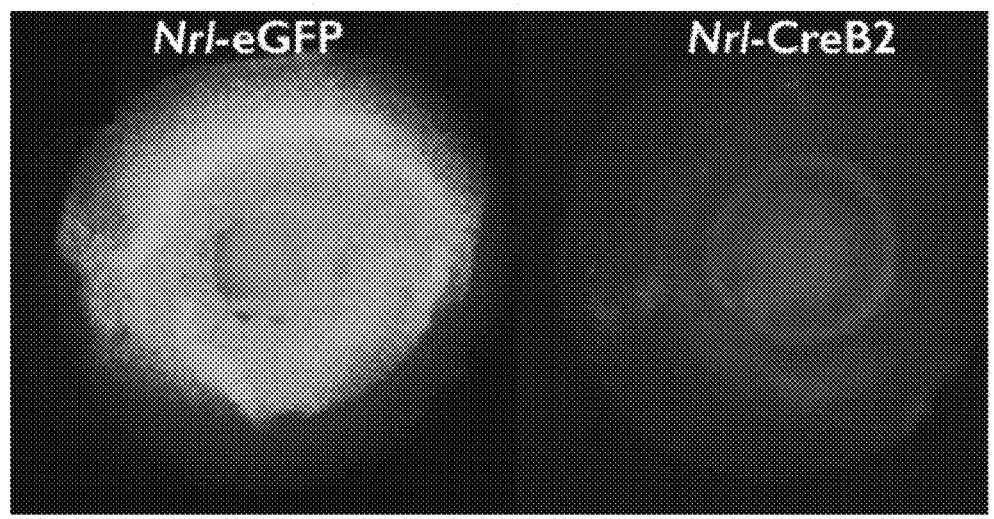
Figure 5D:
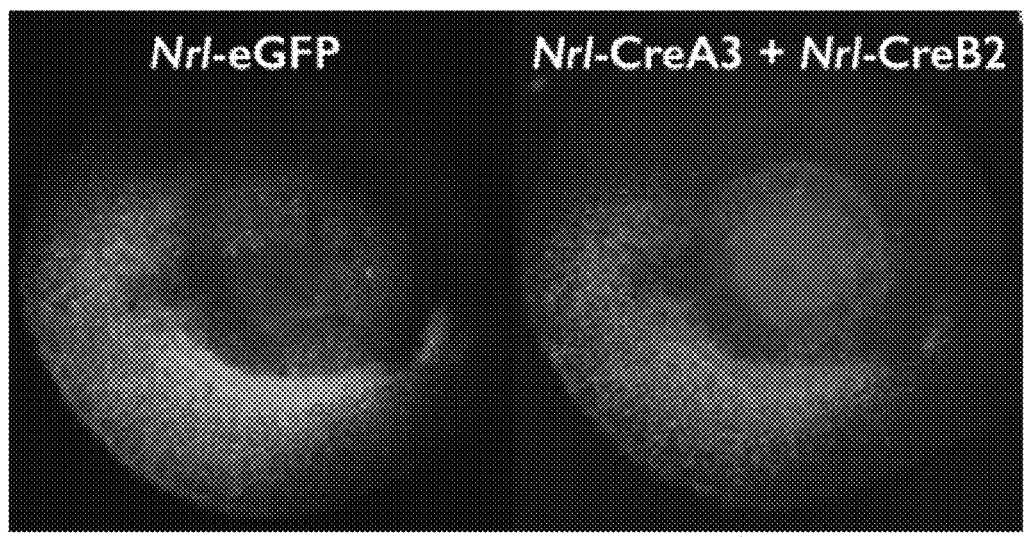
Figure 5E:
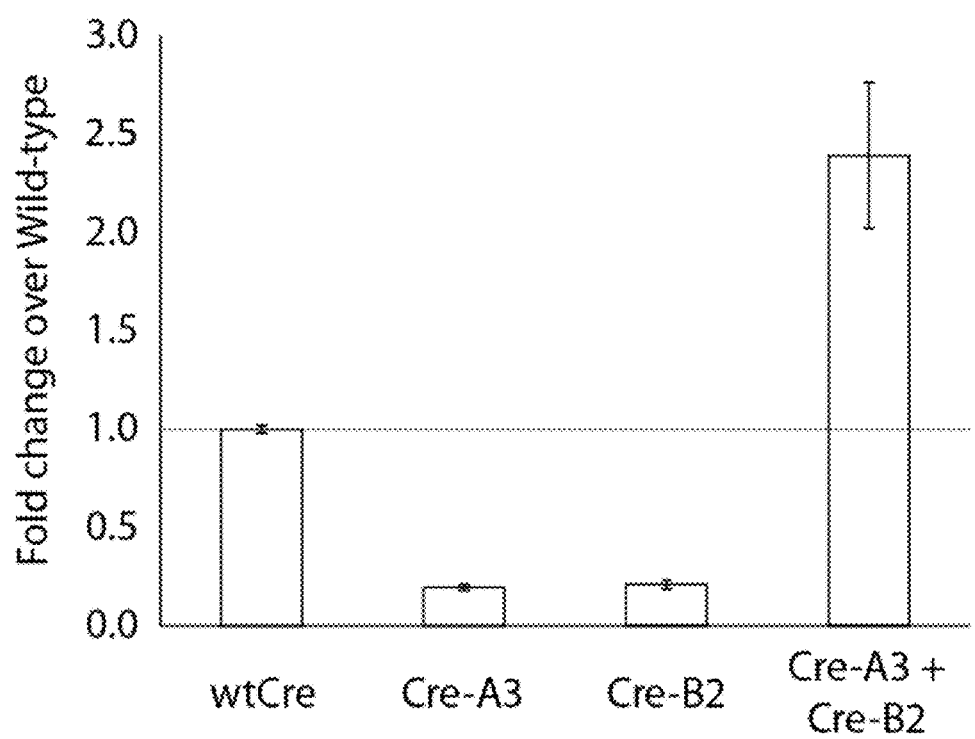
Figure 7A:
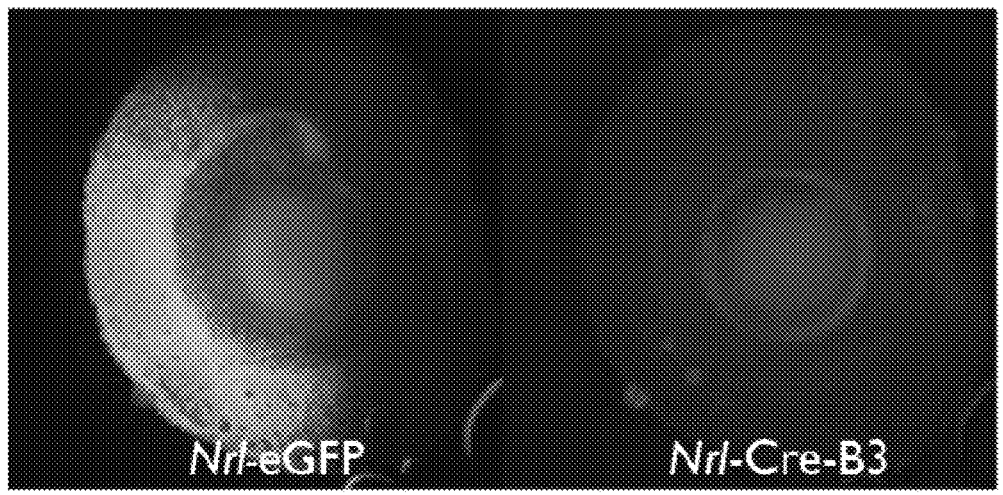
FIG. 7A and FIG. 7B depict images showing Cre activity in retinal explants. Retinal explants were electroporated with vectors containing a gene for Nrl-eGFP as a control for electroporation efficiency, a reporter construct for Cre activity comprised of DsRed preceded by a floxed stop codon, and a gene encoding either wild-type or engineered Cre under control of the Nrl promoter.
Figure 7B:
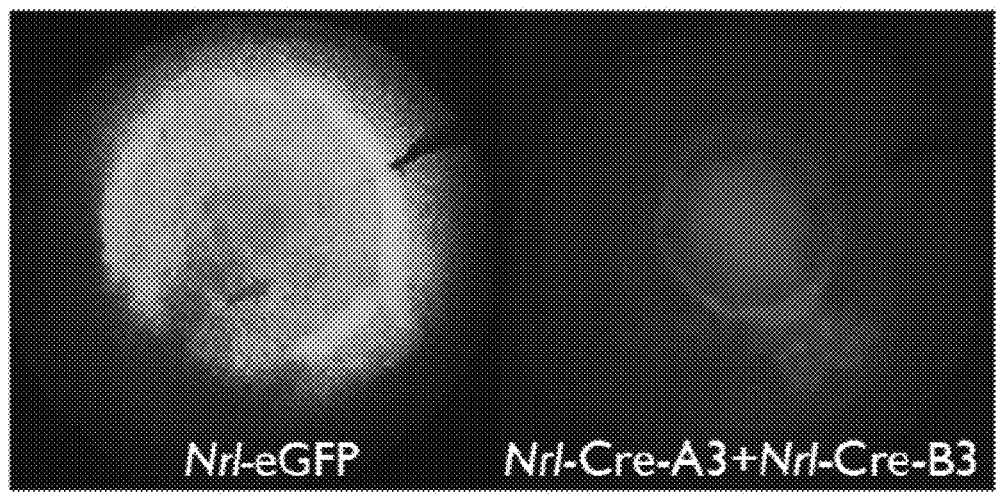

We also evaluated the activity of the Cre mutants in mouse retinal explants. Dissected newborn mouse retinas were electroporated with a construct expressing GFP under the control of the rod photoreceptor-specific Nrl promoter {Akimoto et al., 2006, Proc Natl Acad Sci USA, 103, 3890-5} (as a loading control), Cre mutants under the control of the same Nrl promoter, and a floxed tdTomato reporter construct. After eight days in explant culture, the retinas were harvested, and imaged. The appearance of the flat-mounted retinas under epifluorescent illumination is shown in FIG. 5 and FIG. 7. GFP fluorescence indicates areas of successful electroporation, and red fluorescence reports recombinase activity. Wild-type Cre shows robust activity, with all green cells also exhibiting red fluorescence (FIG. 5A). The Cre-A3 and Cre-B2 mutants alone show very little activity (FIG. 5B-C), while combining the two restores robust activity (FIG. 5D). Quantification confirms that Cre-A3 and Cre-B2 form an obligate heterotetrameric pair in photoreceptor cells (FIG. 5E).

Discussion for the Examples

We sought to engineer a pair of mutants of Cre recombinase that form an obligate ABAB heterotetrameric complex. The Cre-A3 and Cre-B2 mutants are the result of an iterative process of computational and rational protein engineering. We have shown that the two mutants are inactive in isolation, but are functional when combined. Furthermore, we have shown that when additional mutations are used to confer an altered DNA specificity upon either one of the mutants, the arrangements of half-sites that are recombined are consistent with the formation of an ABAB complex. Although our attempts to confirm the nature of the functional complex directly via crystallography were unsuccessful, our data are strongly suggestive that we have succeeded in our goal.

Engineering a novel interface for Cre recombinase monomers that is incompatible with the wild-type interface involves two distinct requirements, one positive and one negative. The positive requirement is that the novel interface must give rise to a functional tetrameric complex. The negative requirement is that any combination of wild-type and engineered monomer surfaces must be functionally incompatible. We found that the negative engineering goal was more difficult to achieve. We were able to generate a novel functional interface using straightforward computational protein design. A previous effort to create a heterotetrameric Cre complex by concerted small-to-large and large-to-small hydrophobic mutations yielded similar results {Gelato et al., 2008, J Mol Biol, 378, 653=665}; the engineered interface was functional, but one of the mutant surfaces retained significant activity in complex with the complementary wild-type surface. We found that additional rounds of rational design were required to reduce the residual activity of homotetrameric complexes.

Previously it has been shown that Cre recombinase can be split into N- and C-terminal fragments (split-Cre) that can reconstitute a functional complex when co-expressed in vivo by virtue of coiled coil dimerization tags appended to each fragment {Hirrlinger et al., 2009, PLoS One, 4, e4286}. The motivation for this approach was to place the split-Cre fragments under different promoters, yielding enhanced control over the cell types in which functional Cre complexes are present and resulting in highly specific conditional gene regulation. However, this approach to splitting Cre is not suitable for our purpose of combining monomers with different DNA specificities. Each split-Cre complex retains specificity for the loxP RT site. Even if specificities of the DNA-contacting regions are altered, the assembly of N and C-terminal fragments is uncontrolled, allowing for multiple combinations of half-site RT site specificities {Saraf-Levy et al., 2006, Bioorganic & medicinal chemistry, 14, 3081-3089}, and making this decomposition unsuitable for targeting asymmetric sites with high specificity.

CRISPR-based systems have emerged as an attractive tool for genome engineering due to the ease with which the Cas9 nuclease can be redirected to arbitrary targets {Cong et al., 2013, Science, 339, 819-23; Jinek et al., 2012, Science; Mali et al., 2013, Science, 339, 823-6}. CRISPR/Cas technology represents the logical conclusion of modular DSB inducing agents, largely rendering ZFN and TALEN approaches obsolete. The Cas9 nuclease can be targeted to any site that contains a protospacer adjacent motif (PAM) sequence (typically 3-5 bases in length) without mutating the protein itself. In cell culture, this activity can drive the efficient generation of loss-of-function mutants when the DSB is repaired by non-homologous end-joining, or gene conversion when homology-directed repair occurs in the presence of an exogenously provided repair template {Hsu et al., 2014, Cell, 157, 1262-78}. Given these features of CRISPR/Cas systems, what role can mutants of Cre recombinase play in genome engineering applications?

Gene conversion by RMCE possesses advantages over DSB-induced gene conversion that are unique to enzymatically autonomous recombinases. A crucial advantage is that no other cofactors or endogenous cellular machinery are necessary. In particular, this avenue for genome editing does not rely upon the homology-directed DNA repair (HDR) system. The balance between DNA repair via HDR and via non-homologous end-joining (NHEJ) is highly dependent on cell type, and HDR itself is not a significant route for DNA repair in cells that are not replicating {Saleh-Gohari and Helleday, 2004, Nucleic Acids Res, 32, 3683-8; Rothkamm et al., 2003, Mol Cell Biol, 23, 5706-15}. Thus, RMCE approaches may prove to be the only effective route to gene conversion for postmitotic cells, where DSB-induced HDR performs poorly. Furthermore, DSB-stimulated gene conversion is efficient over a relatively short range (~100 bp) {Elliott et al., 1998, Mol Cell Biol, 18, 93-101}. In contrast, cassette-mediated exchange is capable of correcting any mutation that falls within the RT site boundaries. Using RMCE, genetic intervals of >100 kb of DNA have been exchanged, with the size of the interval limited by the size of the donor construct, and not by the method itself {Wallace et al., 2007, Cell, 128, 197-209}.

The disadvantage of targeting mutant recombinases to endogenous sites in a genome is the difficulty with which recombinase DNA specificity is altered. Directed evolution has proven to be successful in generating novel RT specificities, and our results show that in at least one case the mutations that alter DNA specificity are compatible with our mutations for controlling tetramer assembly. However, there is no realistic hope for any retargeting strategy that can rival the speed and ease of retargeting in CRISPR/Cas systems. We anticipate that endogenous site RMCE will be useful when a particular genomic locus is of sufficient interest to merit the effort required to obtain mutant recombinases whose RT specificities bracket the locus, or when there is a need to repeatedly exchange the DNA within the genetic interval. This may be the case when a locus harbors a large number of disease-associated polymorphisms that span several kb, or when a 'promoter bashing' experimental approach is desired in an endogenous context.

We have presented an obligate heterotetrameric pair of Cre recombinase mutants. We have demonstrated that this pair can be used to form functional complexes that can recognize asymmetric RT sites. However, to realize the RMCE approach with maximal control over Cre complex formation, we will require a second pair of recombinase monomers to target the second asymmetric RT site that brackets the genetic cassette. This may be accomplished by engineering two additional Cre monomers that form a second obligate heterotetramer that is incompatible with the mutants we have described here. As this involves a large number of positive and negative constraints on monomer association, we suggest that an easier approach will be to use the knowledge of interacting residues we have identified in this study to direct rational redesign of the interface of a Cre homolog {Karimova et al., 2013, Nucleic Acids Res, 41, e37; Sauer and McDermott, 2004, Nucleic acids research, 32, 6086-6095; Suzuki and Nakayama, 2011, Nucleic acids research, 39, e49-e49}. Although no crystal structures are available for close homologs of Cre, sequence homology between recombinases has been recognized that could assist in generating obligate heterotetrameric mutants {Karimova et al., 2013, Nucleic Acids Res, 41, e37; Nunes-Duby et al., 1998, Nucleic Acids Res, 26, 391-406}. We are currently investigating the feasibility of this approach.

Methods for the Examples

Computational Modeling and Design

We selected the 2.2 Å crystal structure of a Cre-loxP Holliday junction as a template for computational design (PDB code: 1 KBU {Martin et al., 2002, J Mol Biol, 319, 107-27}) The protein design capabilities of Rosetta3 {Leaver-Fay et al., 2011, Methods in enzymology, 487, 545} were used to select amino acids to form an alternative interface between Cre monomers. Amino acid positions 25, 29, 32, 33, 35 from chain A and 69, 72, 76, 119, 123 from chain B were chosen for redesign because they form multiple interactions across the largest region of contact between monomers, but do not participate in the protein-DNA interface (FIG. 2). At each of these positions, the calculation permitted mutation to a subset of amino acids including positive, negative or non-polar amino acids (AVMLDERK; SEQ ID NO:1). The redesign calculation used the standard RosettaDesign fixed backbone algorithm. Sidechain rotamers were built using a backbone-dependent rotamer library. Extra rotamers sampling additional values for the) $\chi$ 1 and $\chi$2 side chain torsion angles were included in the design calculation (command line options-ex1, -ex2 in Rosetta). The 'soft_rep_design' scoring function was used {Dantas et al., 2007, J Mol Biol, 366, 1209-21} to evaluate the interactions between the rotamers and the fixed backbone, and between rotamers at different positions. The combinatorial search through conformational space was accomplished using a Monte Carlo method with Metropolis acceptance criteria.

Gene Construction and Protein Expression:

A gene encoding wild-type Cre recombinase with an N-terminal Met-His7 tag was constructed from 100 bp overlapping oligonucleotides ordered from Integrated DNA technologies (IDT) and cloned into the pET42a vector. Cre mutants were generated by site-directed mutagenesis. Proteins were expressed in BL21(DE3) star cells at 30° C. using the autoinduction protocol of Studier {Studier, 2005, Protein Expr Purif, 41, 207-234}.

Protein Purification of Cre Recombinase Variants:

Proteins were expressed in BL21(DE3) star cells at 30° C. using the autoinduction protocol of Studier {Studier, 2005, Protein Expr Purif, 41, 207-234}. The cells were harvested by centrifugation after 30 hours. The cell paste was resuspended in 25 mL buffer A (0.7M NaCl, 50 mM Tris-HCl pH7.8, 5 mM Imidazole), lysed by sonication on ice, and separated from cellular debris by centrifugation. The filtered supernatant was applied to a HisTrap™ HP column (Amersham) and washed with 30 mL Buffer A. The column was then washed with 20 mL 15% buffer B (0.7M NaCl, 50 mM Tris-HCl pH7.8, 500 mM Imidazole). Cre was eluted with a linear gradient from 15% buffer B to 100% buffer B, with the elution peak starting at roughly 20% buffer B. Approximately 10 mL of the eluted protein was collected and dialyzed overnight at 4° C. against 5 L dialysis buffer (0.7 mM NaCl, 50 mM Tris-HCl pH7.8). The protein concentration was then determined by UV absorbance using an extinction coefficient at 280 nm of 49 $mM^{-1}$ $cm^{-1}$. The protein retained activity for months when stored at 4° C.

In Vitro Recombinase Activity Assay:

Two direct loxP repeats or other variants of loxP/M7 sites separated by a ~0.5 kb spacer were cloned between the XbaI and SphI sites of the pBAD33 plasmid. The 0.7 kb DNA substrate for in vitro recombination assays was generated by PCR amplification with pBAD-forward and pBAD-reverse primers. 1 μg of the DNA substrate was incubated with 1 μM Cre in 50 mM Tris-Cl, pH 7.8, 50 mM NaCl and 10 mM MgCl2 for 12 hours at 37° C. Reactions were stopped by incubation at 98° C. for 20 minutes. Reactions were analyzed on 2% agarose gels and visualized by staining with Gel Code Green.

Cell Culture and Transfection:

The plasmid pGL4.23 containing a multiple cloning site (MCS) for insertion of a response element of interest upstream of a minimal promoter and a gene encoding luc2 was purchased from Promega. The original minimal promoter in pGL4.23 was replaced with the haemoglobin beta (HBB) gene minimal promoter 144 bp upstream of the HBB transcription start site. The HBB minimal promoter has only the basic components for transcription (i.e. TATA (SEQ ID NO:2) box and GC box) and was amplified by PCR from mouse genomic DNA. The coding sequence of luc2 in PGL4.23 gene was replaced with different mutants of Cre recombinase using Gibson assembly. The enhancer candidates (CMV and SP1 enhancers) were then cloned into the MCS upstream of the minimal promoter. The engineered plasmids were isolated using standard molecular biology techniques and were confirmed by Sanger sequencing.

Ai14 mouse embryonic stem (ES) cells were engineered by targeted insertion of a construct containing the CAG promoter, followed by a floxed stop cassette-controlled red fluorescent marker gene (tdTomato or RFP) (FIG. 4A). The Ai14 mouse ES cells were cultured in complete media consisting of Dulbecco's modified eagle media (DMEM; Gibco) supplemented with 10% new born calf serum, 10% fetal bovine serum (FBS; Gibco), and 0.3 mM of each of the following nucleosides: adenosine, guanosine, cytosine, thymidine, and uridine (Sigma-Aldrich). To maintain their undifferentiated state, the cells were also cultured in flasks coated with a 0.1% gelatin solution (Sigma-Aldrich) in the presence of 1000 U/mL leukemia inhibitory factor (LIF; Chemicon) and 20 mM β-mercaptoethanol (BME; Invitrogen).

Plasmids used for transfection of cells were prepared using EndoFree Plasmid Maxi Kits (Qiagen). About $2×10^5$ Ai14 ESCs were plated in one well of a six-well plate one day prior to transfection with complete medium plus LIF in feeder free conditions. The cells were then transfected at 70% confluence with a total of 1 μg of plasmid DNA by Lipofectamine 2000 (Invitrogen). The medium was replaced with fresh ESC medium plus LIF the following day and cells were cultured for another day before harvested for fluorescence activated cell sorting (FACS).

Flow Cytometry:

Upon reaching approximately 100% confluence, the cells were trypsinized from the plate and were suspended in Hank's Balanced Salt Solution (HBSS) supplemented with 2 mM EDTA, washed once with PBS, and resuspended in 500 μl PBS. Cellular fluorescence was analyzed on an iCyt Reflection HAPS2 cell sorter at the Washington University Siteman Flow Cytometry Core. Cells were treated with propidium iodide (2 μg/ml) prior to sorting to counter-select dead cells. The gate was set relative to cells transfected with plasmids lacking red fluorescent protein genes (negative controls) to eliminate nonspecific background reporting. A minimum of 7000 total cells was analyzed from each FACS and post-sort analysis was performed with FlowJo software to obtain the percentage of RFP positive cells.

Recombinase Assay in Mouse Retinal Explants:

Electroporations and explant cultures were performed as previously described {Hsiau et al., 2007, PLoS One, 2, e643}. Retinal explants were electroporated in a chamber containing 0.5 μg/mL each of supercoiled DNA encoding a gene for Nrl-eGFP as a control for electroporation efficiency, a reporter construct for Cre activity comprised of DsRed preceded by a floxed stop codon, and a gene encoding either wild-type or engineered Cre under control of the Nrl promoter {Akimoto et al., 2006, Proc Natl Acad Sci USA, 103, 3890-5}. Quantification of fluorescence in retinal explants was accomplished using the ImageJ program (rsbweb.nih.gov/ij/) using a previously described protocol {Montana et al., 2013, Methods Mol Biol, 935, 329=40}.

What is claimed is:

1. An isolated enzyme comprising two distinct subunits A and B, wherein the A subunit comprises one or more mutations at K25, D29, R32, D33, Q35, E123 and R337 relative to SEQ ID NO:1 and the B subunit comprises one or more mutations at E69, R72, L76, E123, and E308 relative to SEQ ID NO:1, wherein if subunit A comprises E123Q, then subunit B does not comprise E123Q and if subunit B comprises E123Q, then subunit A does not comprise E123Q; wherein subunit A comprises at least 80% identity to SEQ ID NO:2 comprising one or more mutations at K25, D29, R32, D33, Q35, E123 and R337 relative to SEQ ID NO:1 and subunit B comprises at least 80% identity to SEQ ID NO:3 comprising one or more mutations at E69, R72, L76, E123, and E308 relative to SEQ ID NO:1; and wherein the isolated enzyme is a tetramer having Cre recombinase activity.

2. The isolated enzyme of claim 1, wherein in subunit A, K25 is mutated to another positive amino acid, D29 is mutated to a positive amino acid, R32 is mutated to a negative amino acid, D33 is mutated to a neutral amino acid, Q35 is mutated to a positive amino acid, E123 is mutated to a neutral amino acid, and/or R337 is mutated to a negative amino acid and in subunit B, E69 is mutated to aspartic acid (D), R72 is mutated to histidine (H) or lysine (K), L76 is mutated to a negative amino acid, E123 is mutated to a neutral amino acid, and/or E308 is mutated to a positive amino acid.

3. The isolated enzyme of claim 1, wherein in subunit A, D29 is mutated to a positive amino acid, R32 is mutated to a negative amino acid, and R337 is mutated to a negative amino acid and in subunit B, E308 is mutated to a positive amino acid.

4. The isolated enzyme of claim 1, wherein subunit A comprises the mutations: K25R, D29R, R32E, D33L, Q35R, E123L and R337E relative to SEQ ID NO:1 and subunit B comprises E69D, R72K, L76E and E308R relative to SEQ ID NO:1.

5. The isolated enzyme of claim 1, wherein subunit A comprises at least 90% identity to SEQ ID NO:2.

6. The isolated enzyme of claim 1, wherein subunit B comprises at least 90% identity to SEQ ID NO:3.

7. The isolated enzyme of claim 1, wherein the isolated enzyme comprises two A subunits and two B subunits.

8. The isolated enzyme of claim 1, wherein the isolated enzyme is a Cre recombinase.

9. The isolated enzyme of claim 4, wherein subunit B further comprises an E123L mutation.

10. The isolated enzyme of claim 1, wherein the isolated enzyme is capable of mediating a site-specific recombination between two predetermined recombination sites, wherein the recombination sites are asymmetric recombination sites comprising two non-palindromic halves flanking a spacer region.

11. The isolated enzyme of claim 10, wherein one non-palindromic half is a loxP site.

12. The isolated enzyme of claim 10, wherein one non-palindromic half is not a loxP site.

13. The isolated enzyme of claim 10, wherein one non-palindromic half is a loxP site and one non-palindromic half is a M7 site.

14. A recombinant vector encoding at least one polypeptide, the polypeptide comprising subunit A comprising one or more mutations at K25, D29, R32, D33, Q35, E123 and R337 relative to SEQ ID NO:1, subunit B comprising one or more mutations at E69, R72, L76, E123, E308 relative to SEQ ID NO:1, or combinations thereof, wherein if subunit A comprises E123Q, then subunit B does not comprise E123Q and if subunit B comprises E123Q, then subunit A does not comprise E123Q; wherein subunit A comprises at least 80% identity to SEQ ID NO:2 comprising one or more mutations at K25, D29, R32, D33, Q35, E123 and R337 relative to SEQ ID NO:1 and subunit B comprises at least 80% identity to SEQ ID NO:3 comprising one or more mutations at E69, R72, L76, E123, and E308 relative to SEQ ID NO:1; wherein the recombinant vector expresses the polypeptide and is selected from the group consisting of: a naked plasmid, a plasmid within a liposome, a retroviral vector, an AAV vector, or a recombinant adenoviral vector.

15. The isolated polynucleotide of claim 14, wherein expression of the polypeptide is driven by a promoter selected from the group consisting of the Nrl (rod photoreceptor-specific) promoter and the HBB (haemoglobin beta) promoter.

16. The isolated polynucleotide of claim 15, wherein expression of the polypeptide is further driven by an enhancer selected from the group consisting of the CMV enhancer and the SP1 enhancer.

17. A host cell comprising the polynucleotide of claim 14.

18. A composition comprising the polynucleotide of claim 14.

19. A method for mediating asymmetric site-specific recombination in a nucleic acid, the method comprising contacting an isolated enzyme of claim 1 with a nucleic acid, wherein the isolated enzyme recognizes asymmetric sites on the nucleic acid and cleaves the asymmetric sites, wherein the asymmetric sites are loxp+M7 asymmetric recombination sites and wherein the asymmetric site-specific recombination is selected from the group consisting of inversion, excision, insertion and translocation.

20. A method for mediating recombination-mediated cassette exchange (RMCE) in a cell, the method comprising contacting an isolated enzyme of claim 1 and an exogenous DNA molecule with a cellular endogenous genome, wherein the isolated enzyme recognizes asymmetric sites on the cellular endogenous genome, wherein the asymmetric sites are loxp+M7 asymmetric recombination sites and wherein the RMCE occurs between the cellular endogenous genome and the exogenous DNA molecule such that the exogenous DNA molecule is integrated by recombination between the two asymmetric sites into a predetermined locus within the cellular genome.

* * * * *